US009555265B2

(12) United States Patent
Schulte

(10) Patent No.: US 9,555,265 B2
(45) Date of Patent: Jan. 31, 2017

(54) INTENSITY-MODULATED ION THERAPY

(71) Applicant: Loma Linda University Medical Center, Loma Linda, CA (US)

(72) Inventor: Reinhard W. Schulte, Grand Terrace, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 14/945,214

(22) Filed: Nov. 18, 2015

(65) Prior Publication Data
US 2016/0144201 A1   May 26, 2016

Related U.S. Application Data

(63) Continuation of application No. 14/171,490, filed on Feb. 3, 2014, now Pat. No. 9,220,920, which is a
(Continued)

(51) Int. Cl.
*A61N 5/10* (2006.01)
(52) U.S. Cl.
CPC .......... *A61N 5/1039* (2013.01); *A61N 5/1031* (2013.01); *A61N 5/1077* (2013.01); *A61N 2005/1087* (2013.01)
(58) Field of Classification Search
CPC .............. A61N 2005/1087; A61N 5/1031; A61N 5/1039; A61N 5/1077; G01N 2223/419; G01N 23/00; G01N 23/046; G01T 1/29; G21K 2201/00
See application file for complete search history.

(56) References Cited

U.S. PATENT DOCUMENTS 3,777,124 A    12/1973  Pavkovich
3,783,251 A    1/1974   Pavkovich
(Continued)

FOREIGN PATENT DOCUMENTS

DE         3 643 893        6/1988
DE     10 2005 034 912      2/2007
(Continued)

OTHER PUBLICATIONS

Archambeau et al., "Conceptual Design of a Proton Therapy Synchrotron for Loma Linda University Medical Center," Fermi National Accelerator Laboratory, Jun. 1986, in 106 pages.
(Continued)

*Primary Examiner* — Edward Park
(74) *Attorney, Agent, or Firm* — Knobbe, Martens, Olson & Bear LLP

(57) ABSTRACT

The therapeutic treatment of a patient using intensity-modulated proton therapy is described. In one example, a method of creating a proton treatment plan is presented that divides volumes of interest into sub-volumes, applies dose constraints to the sub-volumes, finds one or more feasible configurations of a proton therapy system, and selects a proton beam configuration that improves or optimizes one or more aspects of proton therapy. In some implementations, the method of dividing volumes into sub-volumes includes creating fractional sub-volumes based at least in part on proximity to a target volume boundary. In some implementations, the method of finding an improved or optimal proton beam configuration from a set of feasible configurations includes finding a minimum of a cost function that utilizes weighting factors associated with treatment sites.

13 Claims, 14 Drawing Sheets

Related U.S. Application Data continuation of application No. 13/705,903, filed on Dec. 5, 2012, now Pat. No. 8,644,571.

(60) Provisional application No. 61/567,126, filed on Dec. 6, 2011, provisional application No. 61/706,702, filed on Sep. 27, 2012.

(56) References Cited

U.S. PATENT DOCUMENTS

| | | | |
|---|---|---|---|
| 3,852,610 A | 12/1974 | McIntyre |
| 3,942,012 A | 3/1976 | Boux |
| 3,955,089 A | 5/1976 | McIntyre et al. |
| 3,975,640 A | 8/1976 | Boux et al. |
| 3,986,026 A | 10/1976 | Martin |
| 4,020,356 A | 4/1977 | Brahme |
| 4,069,457 A | 1/1978 | Martin et al. |
| 4,095,114 A | 6/1978 | Taumann |
| 4,112,306 A | 9/1978 | Nunan |
| 4,140,129 A | 2/1979 | Heinz et al. |
| 4,230,129 A | 10/1980 | LeVeen |
| 4,378,813 A | 4/1983 | Lovelace et al. |
| 4,442,352 A | 4/1984 | Brahme |
| 4,705,955 A | 11/1987 | Mileikowsky |
| 4,726,046 A | 2/1988 | Nunan |
| 4,827,491 A | 5/1989 | Barish |
| 4,831,254 A | 5/1989 | Jenkins |
| 4,845,370 A | 7/1989 | Thompson et al. |
| 4,868,843 A | 9/1989 | Nunan |
| 5,017,789 A | 5/1991 | Young et al. |
| 5,027,818 A | 7/1991 | Bova et al. |
| 5,037,374 A | 8/1991 | Carol |
| 5,039,861 A | 8/1991 | Swenson |
| 5,039,867 A | 8/1991 | Nishihara et al. |
| 5,107,839 A | 4/1992 | Houdek et al. |
| 5,115,391 A | 5/1992 | Puthenpura et al. |
| 5,117,829 A | 6/1992 | Miller et al. |
| 5,206,893 A | 4/1993 | Hara |
| 5,242,455 A | 9/1993 | Skeens et al. |
| 5,278,886 A | 1/1994 | Kobiki et al. |
| 5,297,037 A | 3/1994 | Ifuku |
| 5,317,164 A | 5/1994 | Kurokawa |
| 5,343,048 A | 8/1994 | Pastyr |
| 5,427,097 A | 6/1995 | Depp |
| 5,440,133 A | 8/1995 | Moyers et al. |
| 5,446,548 A | 8/1995 | Gerig et al. |
| 5,511,549 A | 4/1996 | Legg et al. |
| 5,521,956 A | 5/1996 | Charpak |
| 5,547,454 A | 8/1996 | Horn et al. |
| 5,585,642 A | 12/1996 | Britton et al. |
| 5,596,199 A | 1/1997 | McNulty et al. |
| 5,596,619 A | 1/1997 | Carol |
| 5,602,892 A | 2/1997 | Llacer |
| 5,668,371 A | 9/1997 | Deasy et al. |
| 5,745,545 A | 4/1998 | Hughes |
| 5,751,781 A | 5/1998 | Brown et al. |
| 5,754,623 A | 5/1998 | Seki |
| 5,760,395 A | 6/1998 | Johnstone |
| 5,769,779 A | 6/1998 | Alderson |
| 5,820,553 A | 10/1998 | Hughes |
| 5,847,403 A | 12/1998 | Hughes et al. |
| 5,851,182 A | 12/1998 | Sahadevan |
| 5,866,912 A | 2/1999 | Slater et al. |
| 6,052,435 A | 4/2000 | Hernandez-Guerra et al. |
| 6,104,779 A | 8/2000 | Shepherd et al. |
| 6,144,875 A | 11/2000 | Schweikard et al. |
| 6,148,272 A | 11/2000 | Bergstrom et al. |
| 6,200,025 B1 | 3/2001 | Rich |
| 6,240,161 B1 | 5/2001 | Siochi |
| 6,275,564 B1 | 8/2001 | Ein-Gal |
| 6,316,776 B1 | 11/2001 | Hiramoto et al. |
| 6,345,114 B1 | 2/2002 | Mackie et al. |
| 6,385,286 B1 | 5/2002 | Fitchard et al. |
| 6,437,513 B1 | 8/2002 | Selzer et al. |
| 6,473,490 B1 | 10/2002 | Siochi |
| 6,577,707 B2 | 6/2003 | Siochi |
| 6,736,831 B1 | 5/2004 | Hartmann et al. |
| 6,757,355 B1 | 6/2004 | Siochi |
| 6,774,383 B2 | 8/2004 | Norimine et al. |
| 6,777,700 B2 | 8/2004 | Yanagisawa et al. |
| 6,795,523 B2 | 9/2004 | Steinberg |
| 6,804,548 B2 | 10/2004 | Takahashi et al. |
| 6,809,325 B2 | 10/2004 | Dahl et al. |
| 6,814,694 B1 | 11/2004 | Pedroni |
| 6,822,244 B2 | 11/2004 | Beloussov et al. |
| 7,084,410 B2 | 8/2006 | Beloussov et al. |
| 7,194,063 B2 | 3/2007 | Dilmanian et al. |
| 7,268,358 B2 | 9/2007 | Ma et al. |
| 7,317,192 B2 | 1/2008 | Ma |
| 7,368,740 B2 | 5/2008 | Beloussov et al. |
| 7,398,309 B2 | 7/2008 | Baumann et al. |
| 7,560,715 B2 | 7/2009 | Pedroni |
| 7,629,598 B2 | 12/2009 | Harada |
| 7,692,168 B2 | 4/2010 | Moriyama et al. |
| 7,755,068 B2 | 7/2010 | Ma et al. |
| 7,791,051 B2 | 9/2010 | Beloussov et al. |
| 7,801,270 B2 | 9/2010 | Nord et al. |
| 7,801,988 B2 | 9/2010 | Baumann et al. |
| 7,807,987 B2 | 10/2010 | Braess |
| 7,820,989 B2 | 10/2010 | Sommer |
| 7,825,388 B2 | 11/2010 | Nihongi et al. |
| 7,834,334 B2 | 11/2010 | Grozinger et al. |
| 7,838,855 B2 | 11/2010 | Fujii |
| 7,903,781 B2 | 3/2011 | Foland et al. |
| 7,920,675 B2 | 4/2011 | Lomax et al. |
| 8,080,801 B2 | 12/2011 | Safai |
| 8,085,899 B2 | 12/2011 | Nord et al. |
| 8,109,865 B2 | 2/2012 | Jackson |
| 8,129,699 B2 | 3/2012 | Balakin |
| 8,129,701 B2 | 3/2012 | Al-Sadah et al. |
| 8,154,001 B2 | 4/2012 | Flynn et al. |
| 8,175,892 B2 | 5/2012 | Kapoor et al. |
| 8,217,373 B2 | 7/2012 | Bert et al. |
| 8,253,121 B2 | 8/2012 | Gnutzmann et al. |
| 8,264,174 B2 | 9/2012 | Liu et al. |
| 8,299,448 B2 | 10/2012 | Bert et al. |
| 8,309,939 B2 | 11/2012 | Harada et al. |
| 8,354,656 B2 | 1/2013 | Beloussov et al. |
| 8,395,131 B2 | 3/2013 | Wu et al. |
| 8,461,559 B2 | 6/2013 | Lomax |
| 8,598,546 B2 | 12/2013 | Bert et al. |
| 8,601,116 B2 | 12/2013 | Baumann et al. |
| 8,737,707 B2 | 5/2014 | Pearlstein et al. |
| 8,750,453 B2 | 6/2014 | Cheng et al. |
| 9,207,193 B2 | 12/2015 | Censor et al. |
| 9,220,920 B2 | 12/2015 | Schulte et al. |
| 9,289,627 B2 * | 3/2016 | Otto ............... A61N 5/1031 |
| 2002/0051513 A1 | 5/2002 | Pugachev et al. |
| 2002/0077545 A1 | 6/2002 | Takahashi et al. |
| 2003/0086527 A1 | 5/2003 | Speiser et al. |
| 2003/0155530 A1 | 8/2003 | Adnani et al. |
| 2004/0098445 A1 | 5/2004 | Baumann et al. |
| 2005/0072940 A1 | 4/2005 | Beloussov et al. |
| 2005/0207531 A1 | 9/2005 | Dempsey et al. |
| 2006/0145088 A1 | 7/2006 | Ma |
| 2006/0166353 A1 | 7/2006 | Alfano et al. |
| 2007/0018121 A1 | 1/2007 | Leyman et al. |
| 2007/0034812 A1 * | 2/2007 | Ma ............... A61N 5/1031 |
| | | | 250/492.21 |
| 2007/0225603 A1 | 9/2007 | Jackson |
| 2008/0067401 A1 | 3/2008 | Harada |
| 2008/0164416 A1 | 7/2008 | Safai |
| 2008/0192892 A1 | 8/2008 | Dilmanian et al. |
| 2008/0228418 A1 | 9/2008 | Green |
| 2008/0237494 A1 | 10/2008 | Beloussov et al. |
| 2008/0237495 A1 | 10/2008 | Grozinger et al. |
| 2008/0260098 A1 | 10/2008 | Al-Sadah et al. |
| 2009/0039256 A1 | 2/2009 | Fujii et al. |
| 2009/0154644 A1 | 6/2009 | Nord et al. |
| 2009/0168960 A1 | 7/2009 | Jongen et al. |
| 2009/0189095 A1 | 7/2009 | Flynn et al. |
| 2009/0212231 A1 | 8/2009 | Hill et al. |
| 2009/0261275 A1 | 10/2009 | Rietzel |
| 2009/0304154 A1 | 12/2009 | Lomax et al. |

(56) References Cited

U.S. PATENT DOCUMENTS

| | | |
|---|---|---|
| 2009/0309046 A1 | 12/2009 | Balakin |
| 2010/0074408 A1 | 3/2010 | Bert et al. |
| 2010/0088339 A1 | 4/2010 | Rietzel et al. |
| 2010/0108903 A1 | 5/2010 | Bert et al. |
| 2010/0171047 A1 | 7/2010 | Matsuda |
| 2010/0187446 A1 | 7/2010 | Dilmaniam et al. |
| 2010/0213394 A1 | 8/2010 | Fieres |
| 2010/0288946 A1 | 11/2010 | Honda et al. |
| 2010/0301235 A1 | 12/2010 | Bert et al. |
| 2011/0101236 A1 | 5/2011 | Cameron et al. |
| 2011/0180731 A1 | 7/2011 | Welsh |
| 2011/0233423 A1 | 9/2011 | Balakin |
| 2011/0238440 A1 | 9/2011 | Leuschner |
| 2011/0297850 A1 | 12/2011 | Claereboudt et al. |
| 2011/0309255 A1 | 12/2011 | Bert et al. |
| 2012/0025076 A1 | 2/2012 | Kraft |
| 2012/0056109 A1 | 3/2012 | Lomax |
| 2012/0136194 A1 | 5/2012 | Zhang et al. |
| 2012/0205557 A1 | 8/2012 | Rinecker |
| 2013/0090549 A1 | 4/2013 | Meltsner et al. |
| 2013/0345489 A1 | 12/2013 | Beloussov |

FOREIGN PATENT DOCUMENTS

| | | |
|---|---|---|
| EP | 0 237 165 | 9/1987 |
| EP | 0 247 449 | 12/1987 |
| EP | 0 586 152 | 3/1994 |
| EP | 1 584 353 | 10/2005 |
| EP | 1 900 392 | 3/2008 |
| EP | 2 030 650 | 3/2009 |
| EP | 2 116 277 | 11/2009 |
| EP | 2 392 383 | 12/2011 |
| EP | 2 420 288 | 2/2012 |
| JP | 1989-209077 | 8/1989 |
| JP | H01-209077 | 8/1989 |
| WO | WO 95/01207 | 1/1995 |
| WO | WO 96/25200 | 8/1996 |
| WO | WO 00/16342 | 3/2000 |
| WO | WO 01/00276 | 1/2001 |
| WO | WO 03/020196 | 3/2003 |
| WO | WO 2004/109717 | 12/2004 |
| WO | WO 2005/057738 | 6/2005 |
| WO | WO 2005/102453 | 11/2005 |
| WO | WO 2006/060886 | 6/2006 |
| WO | WO 2006/094533 | 9/2006 |
| WO | WO 2007/012646 | 2/2007 |
| WO | WO 2008/003526 | 1/2008 |
| WO | WO 2008/003527 | 1/2008 |
| WO | WO 2008/106483 | 9/2008 |
| WO | WO 2008/106496 | 9/2008 |
| WO | WO 2009/135879 | 11/2009 |
| WO | WO 2009/142546 | 11/2009 |
| WO | WO 2010/043340 | 4/2010 |
| WO | WO 2010/049071 | 5/2010 |
| WO | WO 2010/101489 | 9/2010 |
| WO | WO 2010/105858 | 9/2010 |
| WO | WO 2010/149740 | 12/2010 |
| WO | WO 2011/091104 | 7/2011 |
| WO | WO 2011/126805 | 10/2011 |
| WO | WO 2011/139863 | 11/2011 |
| WO | WO 2011/154853 | 12/2011 |
| WO | WO 2011/162851 | 12/2011 |
| WO | WO 2012/024448 | 2/2012 |

OTHER PUBLICATIONS

Archambeau et al., "Design of a Proton Therapy Synchrotron," Fermi National Accelerator Laboratory, Jun. 1986, pp. LL467-LL574 in 54 pages.

Brahme, et al.: "Optimization of Proton and Heavy Ion Therapy Using an Adaptive Inversion Algorithm", Radiotherapy and Oncology, vol. 15, Jun. 1989, pp. 189-197.

Chi-square test, 1995, 3 pages. In Dictionary of Economics, Wiley. Retrieved online on Nov. 28, 2012 from <<http://www.credoreference.com/entry/ wileyecon/chi_square_test>>.

Cole et al., "Proceedings of a Medical Workshop on Accelerators for Charged-Particle Beam Therapy" by Fermilab, Jan. 24-25, 1985, LL33170-LL33313 in 144 pages.

Coutrakon, G. et al., "A Prototype Beam Delivery System for the Proton Medical Accelerator at Loma Linda", Medical Physics, vol. 18, No. 6, Nov./Dec. 1991.

Cuperus et al.: "Automatic Generation of Configuration Files for a Distributed Control System," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996. S. 148-153.

Davidi, R., et al., Perturbation-resilient Block-iterative Projection Methods with Application to Image Reconstruction from Projections, International Transactions in Operational Research, vol. 16, pp. 505-524, Feb. 11, 2009.

Final Rejection for U.S. Appl. No. 13/026,051 (corresponding to U.S. Pat. Pub. No. 2011/0220794), May 11, 2015, in 19 pages.

Flynn et al., "Comparison of intensity modulated x-ray therapy and intensity modulated proton therapy for selective subvolume boosting: a phantom study," Phys. Med. Biol., vol. 52, Oct. 21, 2007, pp. 6073-6091.

Gottschalk, "Proton Radiotherapy Nozzle with Combined Scatterer/Modulator", dated Oct. 1987.

Interview Summary for U.S. Appl. No. 13/026,051 (corresponding to U.S. Pat. Pub. No. 2011/0220794), Apr. 19, 2013, in 3 pages.

Interview Summary for U.S. Appl. No. 13/026,051 (corresponding to U.S. Pat. Pub. No. 2011/0220794), Apr. 8, 2013, in 3 pages.

Interview Summary for U.S. Appl. No. 13/026,051 (corresponding to U.S. Pat. Pub. No. 2011/0220794), Feb. 26, 2015, in 3 pages.

Interview Summary for U.S. Appl. No. 13/026,051 (corresponding to U.S. Pat. Pub. No. 2011/0220794), Jan. 14, 2013, in 3 pages.

Interview Summary for U.S. Appl. No. 13/026,051 (corresponding to U.S. Pat. Pub. No. 2011/0220794), Jan. 25, 2013, in 3 pages.

Interview Summary for U.S. Appl. No. 13/026,051 (corresponding to U.S. Pat. Pub. No. 2011/0220794), Mar. 18, 2015, in 3 pages.

Interview Summary for U.S. Appl. No. 13/026,051 (corresponding to U.S. Pat. Pub. No. 2011/0220794), Mar. 30, 2015, in 3 pages.

Kalet et al., "Designing radiotherapy software components and systems that will work together," Serminars in Radiation Oncology, Saunders, Philadelphia, PA, US, vol. 7, No. 1, Jan. 1997, pp. 11-20, XP005440845 ISSN: 1053-4296.

Katehakis et al.: "A Distributed, Agent-Based Architecture for the Acquisition, Management, Archiving and Display of Real-Time Monitoring Data in the Intensive Care Unit," Foundation for Research and Technology, Hellas, Institute of Computer Science, Technical Report [Online] No. 261, Oct. 1999 (Oct. 1999) URL:htollwww.icsJorth.arifkatehaki/oublications/tr261.odf>.

Koehler, et al.: "Flattening of Proton Dose Distributions or Large-Field Radiotherapy", Medical Physics, vol. 4, No. 4, Jul./Aug. 1977, pp. 297-301.

Krause, et al.: "Adaption of a Synchrotron Control System for Heavy Ion Tumor Therapy," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996. S. 14-19.

Krause, et al.: "Re-Engineering of the GSI Control System," Proceedings of the 8th International Conference on Accelerator and Large Experimental Physics Control Systems (ICALEPCS2001), H. Shoace (ed.) San Jose, California, Nov. 27-30, 2001, eConfC011127, WEAT002. S. 219-221.

Laloup, J., "Cancer Therapy Without Side Effects Nearing Trials," dated Apr. 13, 2008 as copied from http://www.wired.com/print/medtech/health/news/2008/04/kanzius therapy on Apr. 23, 2008.

Lalush et al.: "Improving the convergence of iterative filtered backprojection algorithms," Medical Physics, vol. 21, May 1994, pp. 1283-1286.

Li, et al.: "Reconstruction for proton computed tomography by tracing proton trajectories: A Monte Carlo study," Medical Physics, vol. 33, Feb. 2006, pp. 699-706.

(56) References Cited

OTHER PUBLICATIONS

Litt et al. Application of Nonlinear system identification to magnetic resonance imaging and computed tomography. Sep. 1995 IEEE-EMBC and CMBRC, Theme 6: Physiological Systems/Modelling and Identification. pp. 1389-1390.
Marbach, et al.: "Optimization of Field Flatness and Depth-Dose for Therapy Electron Beams", Phys. Med. Biol, vol. 26, No. 3, 1981, pp. 435-443.
Metcalfe et al., "Patient Immobilization and Image Guidance," The Physics of Radiotherapy X-Rays and Electrons, Chapter 12: Jul. 15, 2007, p. 727-764.
Non-Final Rejection for U.S. Appl. No. 13/026,051 (corresponding to U.S. Pat. Pub. No. 2011/0220794), Dec. 5, 2012, in 11 pages.
Non-Final Rejection for U.S. Appl. No. 13/026,051 (corresponding to U.S. Pat. Pub. No. 2011/0220794), Nov. 6, 2014, in 14 pages.
Notice of Allowance dated Mar. 22, 2006 for U.S. Appl. No. 10/994,911.
Notice of Allowance for U.S. Appl. No. 13/026,051 (corresponding to U.S. Pat. Pub. No. 2011/0220794), May 30, 2013, in 9 pages.
Office Action dated Aug. 30, 2005 for U.S. Appl. No. 10/994,911.
Paganetti, et al.: "Proton Beam Radiotherapy—The State of the Art," AAPM 47th Annual Meeting, Seattle, WA, Jul. 25, 2005, in 36 pages.
Penfold, et al., "A more accurate reconstruction system of matrix for quantitative proton computed tomography," Med. Phys. 36 (10), Oct. 2009, pp. 4511-4518.
Product Overview by BrainLAB Radiotherapy Solutions, 2004, BrainLAB AG, in 6 pages.
Proton Therapy Facility: Engineering Design Report, by Fermi National Accelerator Laboratory, Feb. 1987, LL45441-LL45570, in 130 pages.
Pyarali et al.: "Design and Performance of an Object-Oriented Framework for High-Speed Electronic Medical Imaging," Computing Systems, Usenix Association, Berkeley, CA US, vol. 9, No. 4, Jun. 1996, pp. 331-375.
Request for Continued Examination for U.S. Appl. No. 13/026,051 (corresponding to U.S. Pat. Pub. No. 2011/0220794), Aug. 20, 2013, in 3 pages.
Response to Non-Final Office Action for U.S. Appl. No. 13/026,051 (corresponding to U.S. Pat. Pub. No. 2011/0220794), Jan. 28, 2015, in 14 pages.
Response to Non-Final Rejection for U.S. Appl. No. 13/026,051 (corresponding to U.S. Pat. Pub. No. 2011/0220794), May 6, 2013, in 18 pages.
Response to Restriction Requirement for U.S. Appl. No. 13/026,051 (corresponding to U.S. Pat. Pub. No. 2011/0220794), Nov. 19, 2012, in 2 pages.
Restriction Requirement for U.S. Appl. No. 13/026,051 (corresponding to U.S. Pat. Pub. No. 2011/0220794), Sep. 20, 2012, in 10 pages.
Sadrozinski et al., Issues in Proton Computed Tomography, Nuclear Instruments and Methods in Physics Research A 511, Jun. 2003, pp. 275-281, in 7 pages.
Schulte et al., Nanoparticle-Enhanced Proton Computed Tomography: A Monte Carlo Simulation Study, Biomedical Imaging: Nano to Macro, 2004, IEEE International Symposium, Apr. 15-18, 2004, pp. 1354-1356 in 3 pages.
Sidky, E.Y., et al., Image Reconstruction in Circular Cone-Beam Computed Tomography by Constrained, Total-variation Minimization, Physics in Medicine and Biology, vol. 53, (17), 4777-4807, Aug. 13, 2008.
Steckner et al. Computing the modulation transfer function of a magnetic resonance imager. Medical Physics, Mar. 1994, vol. 21, pp. 483-489.
Supplemental Amendment for U.S. Appl. No. 13/026,051 (corresponding to U.S. Pat. Pub. No. 2011/0220794), Mar. 31, 2015, in 19 pages.
Weigel, et al., "Design and preparation of polymeric scaffolds for tissue engineering", Expert Rev Med Devices, 2006, vol. 3, Issue 6, pp. 835-851.
Yang, et al., "The design of scaffolds for use in tissue engineering. Part II. Rapid Prototyping techniques", Tissue Eng, 2002, vol. 8, Issue 1, pp. 1-11.
Yao, et al.: "Frequency-domain optical imaging of absorption and scattering distributions by a Born iterative method," J. Opt. Soc. Am. A., vol. 14, No. 1/Jan. 1997, pp. 325-342.

\* cited by examiner

INTENSITY-MODULATED ION THERAPY

CROSS-REFERENCE TO RELATED APPLICATIONS

This application is a continuation of U.S. patent application Ser. No. 14/171,490, entitled "Intensity-Modulated Proton Therapy," filed Feb. 3, 2014, which is a continuation of U.S. patent application Ser. No. 13/705,903, entitled "Intensity-Modulated Proton Therapy," filed Dec. 5, 2012 (issued as U.S. Pat. No. 8,644,571 on Feb. 4, 2014), which claims priority to U.S. Prov. Pat. App. No. 61/567,126, filed Dec. 6, 2011, entitled "Systems and Methodologies Related to Intensity-Modulated Proton Therapy," and U.S. Prov. Pat. App. No. 61/706,702, filed Sep. 27, 2012, entitled "Intensity-Modulated Proton Therapy." Each application referenced in this paragraph is expressly incorporated by reference herein in its entirety so as to form part of this specification.

BACKGROUND

Field

This disclosure relates generally to intensity-modulated proton therapy (IMPT), and more particularly to treatment plans for IMPT.

Description of Related Art

Radiation therapy systems can be used to provide treatment to patients suffering a variety of conditions. Radiation therapy can be used to perform selective cell destruction, useful in controlling cancers. To perform radiation therapy, a quantity of radiation can be directed into targeted tissue with the goal of damaging the targeted tissue while limiting or minimizing damage to non-targeted tissue.

Proton therapy is a form of radiation therapy that uses protons to destroy targeted cells. Proton therapy can be an efficacious way to selectively destroy targeted cells because protons have unique dosimetric characteristics compared to other radiation, such as electrons or photons. Protons deposit most of their energy near the end of their path through a tissue, compared to photons, for example, which deposit an exponentially decreasing amount of energy as a function of penetration depth. Thus, a proton therapy system can achieve greater targeted treatment compared to photon-based therapy (e.g., exposing targeted tissue to more radiation and/or healthy tissue to less radiation) because an operator can control a depth of penetration and dose profile of protons by selecting an initial energy of the protons. Proton therapy can be delivered using several techniques, including passive scattering, pencil beam scanning, and intensity-modulated proton therapy.

SUMMARY

Example embodiments described herein have innovative features, no single one of which is indispensable or solely responsible for their desirable attributes. Without limiting the scope of the claims, some of the advantageous features will now be summarized.

In some implementations, method is provided for performing intensity-modulated ion therapy. The method includes obtaining a representation of a patient, the representation comprising information about structures within or on the patient. The method includes identifying a volume of interest in the representation of the patient. The method includes dividing the volume of interest into a plurality of sub-volumes and, for each of the plurality of sub-volumes, setting a dose constraint. Dividing the volume of interest into a plurality of sub-volumes can include dividing the volume of interest into a total number of voxels, identifying one or more features of interest, ordering the voxels according to increasing distance from a nearest feature of interest, and defining a sub-volume as a group of a number of consecutive voxels from the ordered voxels, wherein a ratio of the number of consecutive voxels to the total number of voxels is approximately equal to a selected fractional value for the sub-volume. The method includes determining one or more ion treatment plans that satisfy the dose constraints for each of the plurality of sub-volumes. The method includes selecting an ion treatment plan that satisfies treatment criteria from the one or more ion treatment plans. The method includes delivering ions to the patient based on the selected ion treatment plan. The ions can be protons, carbon ions, or other ions.

BRIEF DESCRIPTION OF THE DRAWINGS

The following drawings and the associated descriptions are provided to illustrate embodiments of the present disclosure and do not limit the scope of the claims.

Figure 1A:
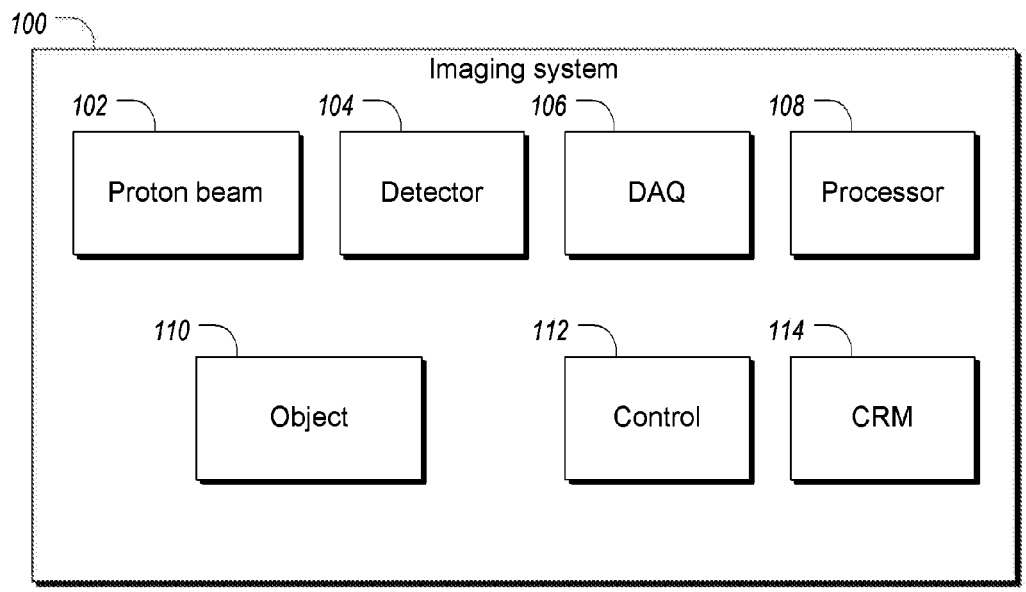
FIG. 1A schematically illustrates that in some implementations, a proton computed tomography (pCT) system can be configured as an imaging system.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements. In addition, where applicable, the first one or two digits of a reference numeral for an element can frequently indicate the figure number in which the element first appears.

DETAILED DESCRIPTION

Although certain embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Described herein are methodologies and related systems for performing intensity-modulated proton therapy. It will be understood that although the description herein is in the context of protons, one or more features of the present disclosure can also be implemented in radiation therapy applications using other ions as well, such as carbon ions. Some embodiments of the methodologies and related systems disclosed herein can be used with various delivery systems, including, for example, intensity modulated spot scanning, distal gradient tracking, distal edge tracking, pencil beam scanning, broad beam or passive scattering, or the like. Some embodiments of the methodologies and related systems can be used to treat a patient or to irradiate an object, and the treatment can be delivered in vivo or in vitro.

Unless explicitly indicated otherwise, terms as used herein will be understood to imply their customary and ordinary meaning. For example, proton beam is a broad term and is to be given its ordinary and customary meaning to a person of ordinary skill in the art (e.g., it is not to be limited to a special or customized meaning), and includes, without limitation, a number of protons of variable energy aimed at a patient or object from a given direction or from multiple directions. For example, a system can deliver a proton beam to a patient by accelerating or receiving accelerated protons, mixing protons of various energies into a single beam, and directing the beam of protons at a patient.

Proton beamlet is a broad term and is to be given its ordinary and customary meaning to a person of ordinary skill in the art, and includes, without limitation, a stream of protons of a given initial energy and direction which can comprise part of a proton beam. For example, a system can accelerate protons to a particular energy using any suitable means, focus the stream of protons into a narrow stream, and direct the stream of protons either to a patient or to a system that can combine multiple proton beamlets into a proton beam.

Proton treatment plan is a broad term and is to be given its ordinary and customary meaning to a person of ordinary skill in the art, and includes, without limitation, a two- or three-dimensional dose distribution generated by one, two, or more than two proton beams. Generally, a proton treatment plan can be overlaid with a treatment planning CT study. For example, a proton treatment plan can include doses to be delivered to volumes of interest within a patient or object. As another example, a proton treatment plan can include a configuration of proton beams or beamlets adapted to deliver a defined, desired, or planned dose distribution to a patient or object.

Proton treatment planning system is a broad term and is to be given its ordinary and customary meaning to a person of ordinary skill in the art, and includes, without limitation, a module, system, computer program, hardware components, instructions on computer readable medium, or any combination of these configured to use a forward problem solver module to calculate a dose distribution in a patient or object given characteristics of a proton beam, tissue composition, or both. For example, a proton treatment planning system can include one or more processors, memory, and/or computer readable medium configured to calculate doses delivered to tissue in a patient based at least in part on proton beam energies, directions, and aiming points of one or more proton beams. As another example, a proton treatment planning system can include a module adapted to calculate proton energy deposition in tissue based at least in part on characteristics of the tissue and properties of the proton beam delivering the protons. As another example, a proton treatment system can include a system or module configured to determine a proton beam configuration suitable for delivering protons to volumes of interest such that doses to the volumes of interest fall within prescribed dose constraints.

Overview of Proton Imagine and Therapy Systems

FIG. 1A shows that in some embodiments, an imaging system 100 can be configured to perform proton computed tomography (pCT) operations and yield data that can be represented as a CT image of one or more portions of an object 110. The imaging system 100 can include a proton beam component 102 configured to deliver a beam of protons to the object 110. Controlling of various parameters of the proton beam, such as energy, direction and intensity can be achieved in a number of known ways.

The imaging system 100 can further include a detector component 104 configured to characterize protons that are incident on the object 110 as well as those that have passed through the object. In some implementations such a detector component 104 can be configured to characterize single protons.

The imaging system 100 can further include a data acquisition (DAQ) component 106 configured to read out signals from the detector component 104 so as to facilitate CT analysis. Amount of signal processing performed by the DAQ component 106 can vary.

In some implementations, signals from various detectors can be converted to digital signals by one or more analog-digital-converters (ADCs), and such digital signals can be read out under the control of a control component 112. Various control parameters such as event triggering, timing of event signals and readout, and resetting of detectors can also be controlled by the control component 112.

In some implementations, the imaging system 100 can further include a processor 108 that is configured to receive the digitized signals and perform analyses such as tracking of protons upstream and downstream of the object 110, as well as calculation of energies of downstream protons that passed through the object 110. In some implementations, tomographic reconstruction processing can also be performed by the processor 108. In other implementations, such tomographic reconstruction processing can be performed by a separate processor.

In some implementations, the imaging system 100 can further include a computer readable medium 114 configured to store information and/or executable instructions that facilitate operation of one or more components of the system 100. In some implementations, the computer readable medium 114 can include information and/or executable instructions that facilitate performance of one or more reconstruction processes. In some implementations, such information and/or executable instructions can be stored in a non-transitory manner.

In some implementations, one or more features of the present disclosure can be incorporated into a radiation therapy system 120 such as a proton or carbon beam therapy system. The therapy system 120 can include a proton or carbon beam component 122 configured to deliver a beam of protons or carbon ions to a patient 130. Such a beam of protons or carbon ions can be configured to yield a therapeutic effect on the patient. In some implementations, the proton beam component 122 can also be configured to yield proton beams that can pass through the patient so as to allow tomographic analysis as described above in reference to FIG. 1A. Examples of how such beams can be provided are described herein in greater detail.

The therapy system 120 can further include a detector component 124 configured to facilitate the treatment utilization of the proton beam 122. Such a detector component 124 can include devices that are configured to characterize protons that are incident on the patient 130 with desired parameters such as energy, direction and intensity. Such devices can be implemented in a number of known ways.

In some implementations, the detector component 124 can further include devices that are configured to facilitate pCT imaging functionalities such as those described in reference to FIG. 1A. In some embodiments, at least some of the therapy related detection devices can also be utilized for the purpose of pCT imaging. For example, beam detectors upstream of the patient can be utilized to characterize individual protons incident on the patient during operation in an imaging mode.

The therapy system 120 can further include data acquisition (DAQ) 126, control 132, processor 128 and computer readable medium 134 components configured to facilitate therapeutic and/or imaging modes of operation. The therapy system 120 can use the control 132, processor, and computer readable medium 134 to solve forward and inverse problems, create treatment plans, determine dose distributions, determine suitable settings to achieve a dose distribution, analyze representations of a patient to determine a treatment plan, receive user input, and the like.

The proton beam 122 of the therapy system 120 can be provided through the use of proton accelerators, such as cyclotrons, synchrotrons, linear accelerators, and the like. The proton beam 122 can be provided from multiple angles and at varying energies. The proton beam 122 can be a single beam of protons or multiple beams delivered in parallel or from multiple directions. In some embodiments, the therapy system 120 includes various components to shape and/or monitor the proton beam 122. For example, the therapy system 120 can include ionization chambers, magnets, scatterers, absorbers, range modulators, apertures, compensators, collimators, and the like.

The therapy system 120 can deliver the proton beam 122 to the patient through various means including broad beam or passive scattering, beam scanning, and/or intensity modulated proton therapy. Active or passive energy modulating components can be used by the therapy system 120 to control the depth of penetration of the proton beam 122. The therapy system 120 can include components configured to control the proton beam shape, direction, orientation, solid angle, fluence, cross-sectional area, and the like. As an example, a passive scattering therapy system can include one or more scattering surfaces to broaden and/or shape the proton beam 122 to deliver a desired dose to a targeted volume. In a beam scanning therapy system, the therapy system 120 can include magnets used to scan or steer the proton beam 122 across a target volume. In an IMPT system, the proton beam 122 can be magnetically and/or mechanically scanned over a target volume where the intensities of the beam spots on the target volume are modulated to deliver a planned or desired dose. In an IMPT system, the proton beam 122 can be delivered from one or more angles and/or positions wherein the intensities of the proton beam 122 at the various angles and/or positions is modulated to deliver a planned or desired dose.

In some embodiments of a therapy system 120, multiple proton beams 122 are delivered to a patient from multiple directions and angles. In some implementations, an individual proton beam comprises multiple proton beamlets where a beamlet is a group of protons with generally the same initial energy and direction. Proton beamlets can be formed using any suitable technique, including through the use of magnetic lenses.

The therapy system 120 can control, configure, or select energy distributions of the proton beams 122. A single proton beam 122 can comprise one or more proton beamlets. A proton beamlet is a group of protons with generally the same initial energy. To control, configure, or select the energy distribution of a proton beam 122, relative intensities of proton beamlets can be chosen such that the desired energy distribution for the proton beam 122 is achieved. The proton beamlets can be selected from a continuous energy range, or they can have discrete energy values. The intensities and/or energies of the proton beamlets can be actively or passively modulated by the therapy system 120. The energy distribution of a proton beam 122 can be configured to produce a SOBP such that structures in the patient 130 receive desirable doses.

The therapy system 120 can be configured to deliver proton beams from one or more angles and/or positions. In some embodiments, the therapy system 120 can have proton beams 122 at fixed relative locations. For example, the proton beams 122 can be coplanar lying along a circle, ellipse, square, rectangle, regular polygon, or other configuration, or the proton beams 122 can be non-coplanar. In some embodiments, the proton beams 122 are distributed along the therapy system 120 in an irregular pattern. In some embodiments, the proton beams 122 are steerable such that an orientation of the proton beam 122 relative to the patient 130 can change before, during, or after operation. Changing orientations for the proton beams 122 can include configuring an angle from which the proton beam 122 will be directed to the patient 130. In some embodiments, the therapy system 120 can dynamically change the positions and/or orientations of the beams 122. In some embodiments, the position of the patient 130 relative to the therapy system 120 can be altered.

Appropriately delivered proton, carbon ion, or other ions can provide a number of benefits in therapeutic applications such as cancer treatments. For example, proton therapy provides a benefit due at least in part to a sharp energy loss at the end of travel of a proton in a given material. Such a sharp energy loss has a relatively sharp peak called a Bragg peak and few of the particles having similar initial beam energy penetrate beyond such a depth. Depth locations of Bragg peaks can depend on the particle beam energy. Generally, a deeper Bragg peak can be achieved by a higher energy particle beam. Protons used for therapy can have energies in a range of about 70 MeV to 250 MeV and carbon ions up to 430 MeV/atomic mass unit.

Figure 2A:
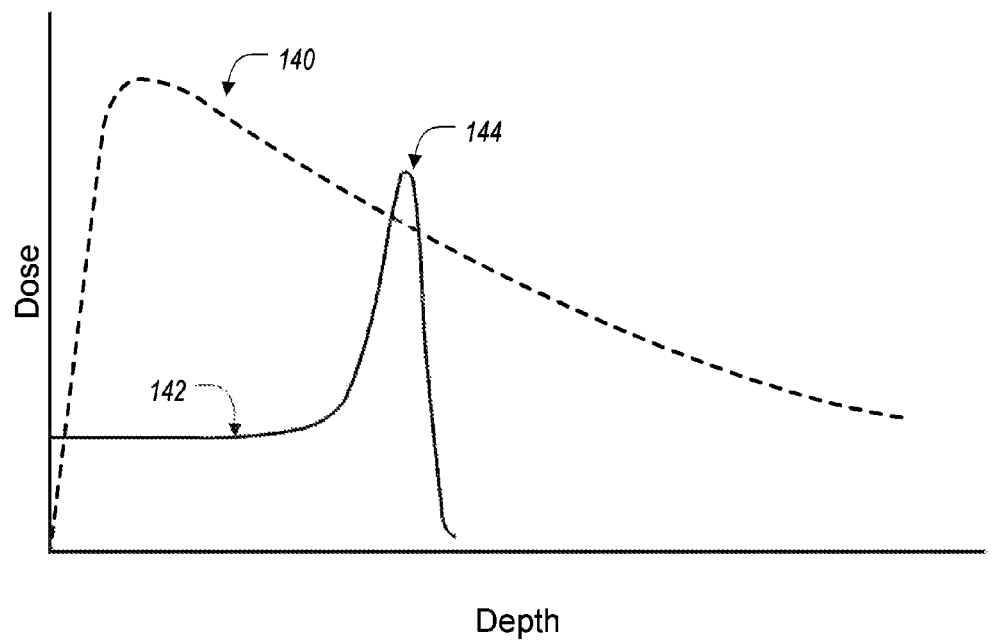
FIGS. 2A and 2B illustrate example dose profiles for photon and proton therapies, where protons can be configured to provide a more selective dose delivery in a desired region being targeted.

FIG. 2A shows an example of a Bragg peak 144 of an energy loss profile 142 as a function of depth as an energetic proton travels in a given material (e.g., tissue). In comparison, a relative dose profile 140 for an electromagnetic radiation (e.g., X-ray or gamma ray) has a relatively sharp rise to a maximum followed by a gradual decrease as a function of depth. Accordingly, photon-based radiation does not provide a similar end-range control provided by use of protons and carbon ions.

Figure 2B:
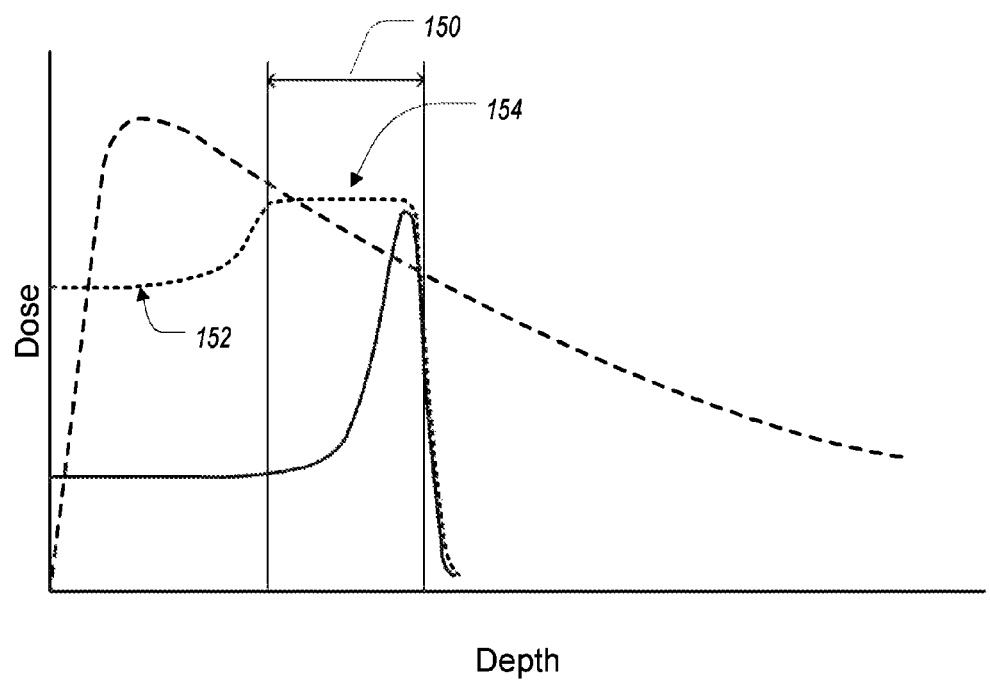

FIG. 2B shows that a plurality of pristine Bragg peaks can combine to yield a spread out Bragg peak (SOBP) 154 in a cumulative dose profile 152. Such pristine Bragg peaks can be achieved by subjecting the same volume with proton beams having different energies. The location of the resulting spread out Bragg peak 154 can be selected to overlap with the depth boundaries of a target region 150. If the beam energies are properly selected, the spread out Bragg peak can fall off sharply beyond the distal boundary of the target region.

Figure 3A:
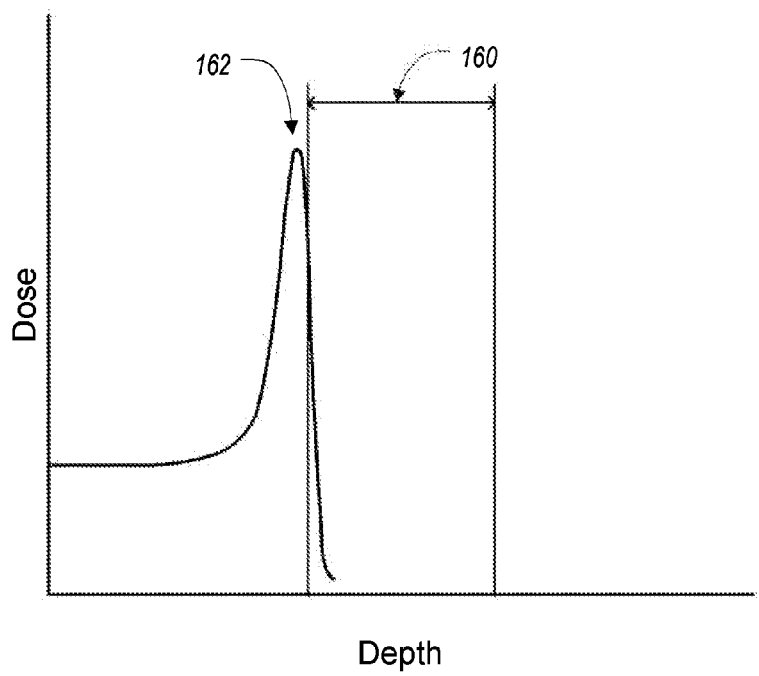
FIGS. 3A and 3B illustrate that wrong calculations of protons' Bragg peak locations relative to the desired target can result in undesirable irradiation of regions outside of the target.
Figure 3B:
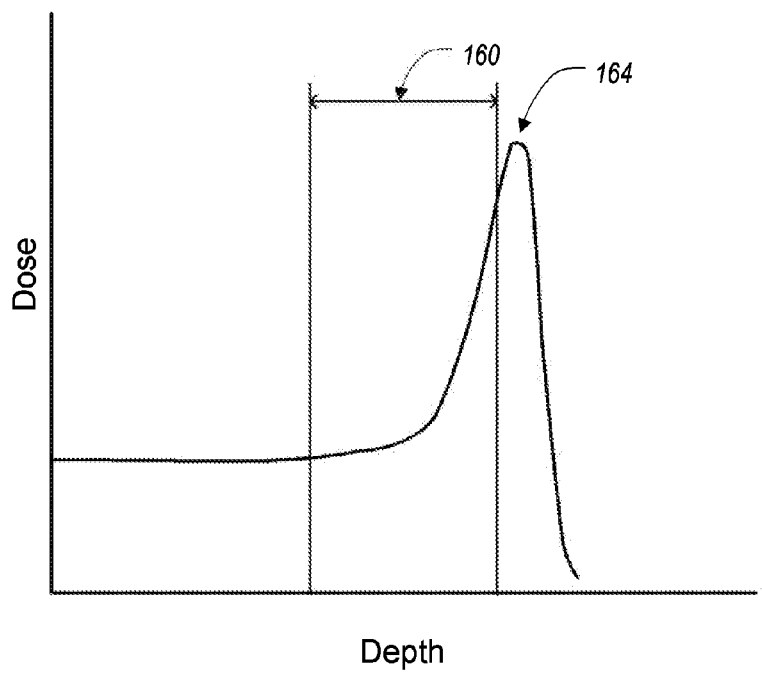

Based on the foregoing, proper matching of depth boundaries of a target region with a spread out Bragg peak can be an important particle therapy consideration. If the distal portion of the spread out Bragg peak is too deep, such as in the example in FIG. 3A, unnecessary and harmful radiation dose (e.g., a substantial portion of a Bragg peak 164) is provided to a region beyond the distal boundary of the target region 160. If the proximal portion of the spread out Bragg peak is too shallow, such as in the example in FIG. 3B, unnecessary extra radiation dose (e.g., a substantial portion of a Bragg peak 162) is provided to a region in front of the proximal boundary of the target region 160. On the other hand, a proximal portion of the spread out Bragg peak that is too deep, and/or a distal portion of the spread out Bragg peak that is too shallow, may result in certain portions of the target region not being irradiated properly.

An operator or physician can characterize a medium in which targeted and/or surrounding structures reside to reduce the dose to non-targeted structures and/or increase the dose to targeted structures. A factor to consider when planning a treatment, then, is the uncertainty of proton penetration depth in the medium. This uncertainty can arise in part from characterizing the medium with a probe radiation different from the therapy radiation that interacts differently with the medium. For example, calculating proton range in a sample using X-ray CT measurements can yield an uncertainty of about 3.5% of a proton's or carbon ion's range. In different portions of a human body, this uncertainty equates to different distances, such as about 3-5 mm in brain and about 10-12 mm in pelvis. Additional uncertainties can be introduced due to the presence of materials with unknown densities, as well as streak artifacts in the X-ray CT images. Using pCT techniques can reduce the range uncertainty to about 1% or less of the proton's range. Some examples of pCT techniques are described in U.S. patent application Ser. No. 13/026,051, entitled "SYSTEMS AND METHODOLOGIES FOR PROTON COMPUTED TOMOGRAPHY," filed Feb. 11, 2011, which is hereby incorporated by reference in its entirety.

Overview of Proton Therapy Methodologies

Figure 4:
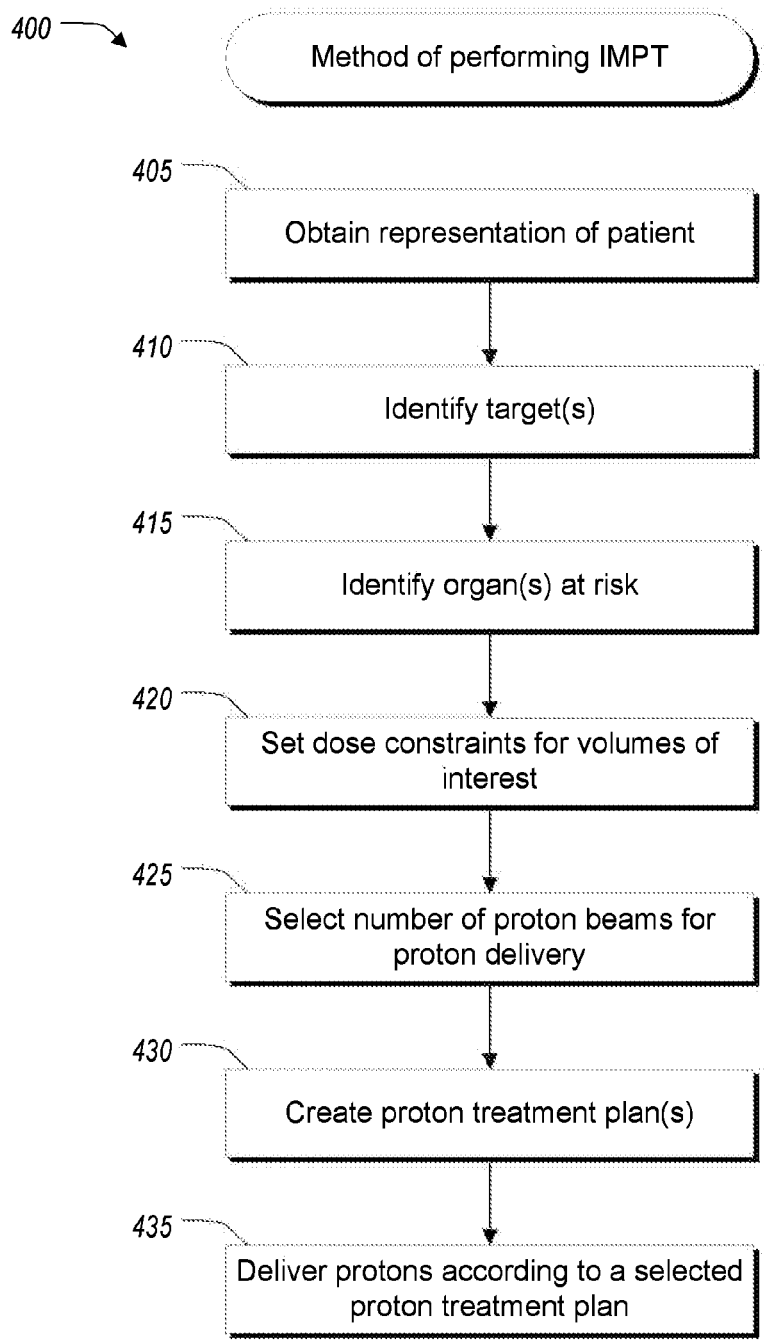
FIG. 4 illustrates a flow chart of an example process that can be implemented to perform proton therapy on a patient.

FIG. 4 illustrates a flow chart of an example method 400 that can be implemented to perform proton therapy on a patient. For ease of description, the process 400 is described as performed by a proton therapy system. The proton therapy system can be a system configured to deliver protons such as the therapy system 120 described herein with reference to FIG. 1B. The proton therapy system can be different from the therapy system 120, including more, fewer, and/or different components. The proton therapy system can include multiple components, each of which can be configured to perform one or more of the steps in the process 400. Each step of the process 400 can be performed by a single component or multiple components. In some embodiments, the proton therapy system includes modules configured to perform one or more steps in the process 400.

In block 405, the proton therapy system obtains a representation of the patient that is to receive proton therapy. The representation can be, for example, one or more digital or analog images, a sequence of images, a video, a representation of densities of the patient as a function of position in the patient, a representation of another biological property of the patient as a function of position, or any combination of these. In some embodiments, the representation is created using functional imaging, such as X-ray CT, proton CT (pCT), positron emission tomography (PET), magnetic resonance imaging (MRI), and/or spectroscopic imaging. As described more fully herein, it can be advantageous to use a representation derived from pCT to reduce possible uncertainties in proton penetration ranges. In some embodiments, the proton therapy system analyzes the obtained representation to create a map or image of structures on and/or within the patient. For example, the proton system can analyze the representation to create a two- or three-dimensional plot of the relative densities of structures on and/or within the patient. In some embodiments, the proton system creates one or more images from the representation which can be presented to a user, oncologist, dosimetrist, physicist, operator, physician, patient, or the like.

In some embodiments, the representation can be used to obtain information related to biological properties of targeted structures and/or surrounding structures. Such biological information can include, for example, composition, clonogen density, tumor hypoxia, proliferation, and/or radiosensitivity. In some implementations, non-uniform dose distributions across a targeted volume can benefit from knowledge of biological information to improve or optimize a treatment plan. Selective targeting of sub-volumes within a target can increase the probability of destroying the targeted cells and/or reduce complications to non-targeted tissues or organs at risk. In some implementations, a substantially uniform dose is desired across the targeted volume.

In block 410, one or more targets can be identified. The target can be any volume that includes cells whose destruction is desired, and can include, for example, cancerous cells, dysplastic cells, tumors, lesions, or other cells or tissue. In some embodiments, the target is automatically identified by the proton therapy system based at least in part on the obtained representation. The proton therapy system can be configured to identify the target based at least in part on one or more criteria such as, for example, location, density, size, temperature, blood flow, oxygenation, shape, other biological properties, other physical properties, or any combination of these. In some embodiments, the proton therapy system receives input from a user to identify the target. Identifying the target can include, for example, indicating which structure, structures, or portion of a structure is the target volume; mapping the target volume; localizing the target volume on or within the patient; extracting biological information about the target volume; or any combination of these.

In some embodiments, identifying the target includes dividing the target volume into sub-volumes. Target sub-volumes can be selected and/or delineated based at least in part on, for example, physical properties, biological properties, practical concerns, geometrical considerations, or any combination of these. The proton therapy system can identify target sub-volumes based at least in part on the obtained representation, biological information, and/or data received from a user. In some embodiments, the proton therapy system identifies the target sub-volumes according to standards set by the International Commission of Radiation Units (ICRU). For example, the Gross Target Volume (GTV) can be defined as the gross palpable, visible, or clinically-demonstrable disease; the Clinical Target Volume (CTV) can include the GTV plus any margin for sub-clinical malignant disease; the Internal Target Volume (ITV) can include the CTV plus an internal margin for organ motion; and the Planning Target Volume (PTV) can include the CTV or the ITV plus any setup margin for uncertainties related to patient positioning and/or alignment of therapeutic beams. In some embodiments, other sub-volume identification schemes are used. For example, a target sub-volume can be defined based at least in part on proton energy deposition characteristics, proximity to an organ at risk, and/or tissue composition.

In block 415, the proton therapy system identifies one or more organs at risk. An organ at risk can include any organ or structure in the patient where cell or tissue destruction is less desirable or would be harmful to the patient. The positions of the identified organs at risk relative to the target volume can be identified and mapped in two or three dimensions through the use of functional imaging. Similar to the identification of the target volume in block 410, the proton therapy system can identify organs at risk automatically, semi-automatically, and/or based at least in part on data received from a user. Identifying organs at risk can include, for example, indicating which structure, structures, or portions of a structure is an organ at risk; mapping the organs at risk; localizing the organs at risk within the patient; extracting biological information about the organs at risk; or any combination of these.

In some embodiments, identifying organs at risk includes dividing the organs at risk into sub-volumes. The sub-volumes of organs at risk can be selected and/or delineated based at least in part on, for example, physical properties, biological properties, practical concerns, geometrical considerations, or any combination of these. The proton therapy system can identify organ at risk sub-volumes based at least in part on the obtained representation, biological information, and/or data received from a user. In some embodiments, the proton therapy system identifies the organ at risk sub-volumes according to standards set by the ICRU. For example, the Organ at Risk (OAR) can be defined as normal tissue or organ whose radiation sensitivity can significantly influence treatment planning and/or prescribed dose wherein the OAR should be delineated in its entirety or within stated anatomical or geometrical boundaries; the Planning OAR Volume (PRV) can include the OAR plus any margin for internal organ motion and/or setup margin for uncertainties related to patient positioning and alignment wherein the PRV should be delineated even where it overlaps PTVs or other PRVs. In some embodiments, other sub-volume identification schemes are used. For example, an organ at risk sub-volume can be defined based at least in part on proton energy deposition characteristics, proximity to a target volume, and/or tissue composition. In some implementations, any volume that is not classified as either a target or an organ at risk can be designated as a Remaining Volume at Risk (RVR).

In block 420, the proton therapy system sets dose constraints for volumes and/or sub-volumes of interest. The volumes and sub-volumes of interest can include target volumes, target sub-volumes, organ at risk volumes, organ at risk sub-volumes, remaining volumes at risk, other volumes, other sub-volumes, or any combination of these. An operator, user, dosimetrist, physicist, oncologist, or physician can use dose constraints to account for tissue tolerance, limit or control the exposure of normal tissue to radiation, specify desired levels of radiation for targeted tissue, and the like. To accomplish one or more of these goals, the proton therapy system can set dose constraints based at least in part on, for example, tissue properties of organs at risk and/or targeted volumes, relative positioning of volumes and sub-volumes, percentage of volume or sub-volume with diseased cells, patient movement, volume of interest variation with time, range uncertainties in proton penetration depth, or any combination of these.

In some embodiments, the proton therapy system selects and sets the dose constraints. In some embodiments, the proton therapy system receives dose constraints from a user, operator, physician, or the like. Dose constraints can be selected based at least in part on a desired therapeutic result or effect, radiosensitivity of the volumes and/or sub-volumes of interest, input from a physician, operating characteristics of the proton therapy system and associated proton beam, proximity and positioning of surrounding structures, avoiding an undesired effect, prescribed standards, nature of targeted cells, properties of targeted cells, or any combination of these. In some embodiments, the proton therapy system sets a maximum dose constraint, a minimum dose constraint, or both for one or more volumes or sub-volumes of interest.

In block 425, the proton therapy system selects a number of proton beams for use in delivering protons to the patient. Proton therapy systems can provide one, two, or more than two proton beams for the treatment of a patient. One or more of the provided proton beams can be selected to perform radiation therapy for a patient. The number of proton beams selected can affect, for example, dose conformity, integral dose, target coverage, or dose to organs at risk. In some implementations, the number of proton beams can be selected to achieve a desired therapeutic result, such as, for example, increasing dose conformity and reducing the integral dose. The number of beams can affect the speed at which the system can create proton treatment plans. The computational speed of a proton treatment system can depend at least in part on the number of selected proton beams as that number corresponds to the number of permutations of different possibilities of energy distributions, directions, and orientations of proton beams. In some implementations, reducing the number of proton beams may be desirable to reduce the time and/or computing power to calculate feasible, desirable, or optimal proton treatment plans. In some implementations, users select a proton treatment plan from plans presented by the proton therapy system. In such a scenario, it can be advantageous to select a number of proton beams such that fewer options are presented to the user to avoid overwhelming the user due to the number of possible plans.

In block 430, the proton therapy system creates a proton treatment plan. The proton treatment plan can include a two- or three-dimensional dose distribution that could be generated by the selected proton beams. The proton therapy system can present the proton treatment plan to a user, operator, dosimetrist, oncologist, physicist, physician, patient, technician, or the like through a display apparatus. In some implementations, the system presents the treatment plan overlaid on the obtained representation. For example, the system can display one or more images obtained from pCT and overlay the dose distribution on the one or more images such that the user can visually analyze the treatment plan. The system can be configured to display, for example, projected doses to volumes and sub-volumes of interest, indicators of the boundaries of volumes and/or sub-volumes of interest, labels identifying volumes and/or sub-volumes of interest, dose volume histograms, treatment plan quality or conformity indicators, or any combination of these.

The proton therapy system can include a forward problem solver module to assist in creating proton treatment plans. The forward problem solver module can be used to calculate a dose distribution in a patient as a function of properties of a proton beamlet. The dose distribution generated by the proton beamlet depends at least in part on the composition of the patient and the energy, orientation, and direction of the proton beamlet. In some implementations, the forward problem solver module incorporates characteristics of proton beamlets that influence the calculated dose distribution. As described more fully herein with reference to FIG. 6, the forward problem solver module can be used to calculate a dose distribution based on multiple proton beamlets, thus generating a proton treatment plan.

The proton therapy system can include an inverse problem solver module to assist in creating proton treatment plans. The inverse problem solver module can be used to calculate a proton beam configuration that attempts to achieve a prescribed dose distribution. Given a prescribed dose distribution, the inverse problem solver module can be configured to generate possible proton beam configurations that satisfy the prescription. The proton beam configurations can include the number of beams, the distribution of proton energies in the beams, the orientation of the beams, the direction of the beams, the duration of therapy, or any combination of these. As described more fully herein with reference to FIGS. 7 and 8, the inverse problem solver module can be used to generate feasible proton treatment plans. A feasible proton treatment plan is a plan that satisfies the dose constraints set in block 420.

In some embodiments, the proton therapy system includes an improvement module for improving or optimizing proton treatment plans. As described more fully herein below, the improvement module can attempt to improve or optimize aspects of one or more proton treatment plans based at least in part on weighted sums of doses, min-max dose functions, Pareto optimality, or any combination of these. In some embodiments, the proton therapy system accepts input from a user to include in the improvement module. For example, the user can choose weighting factors to enhance certain aspects of a treatment plan, such as dose-sparing for normal tissue or increasing tumor control probability, or the weighting factors can be chosen to emphasize a balance between improving the tumor control probability and sparing normal tissue.

Figure 5:
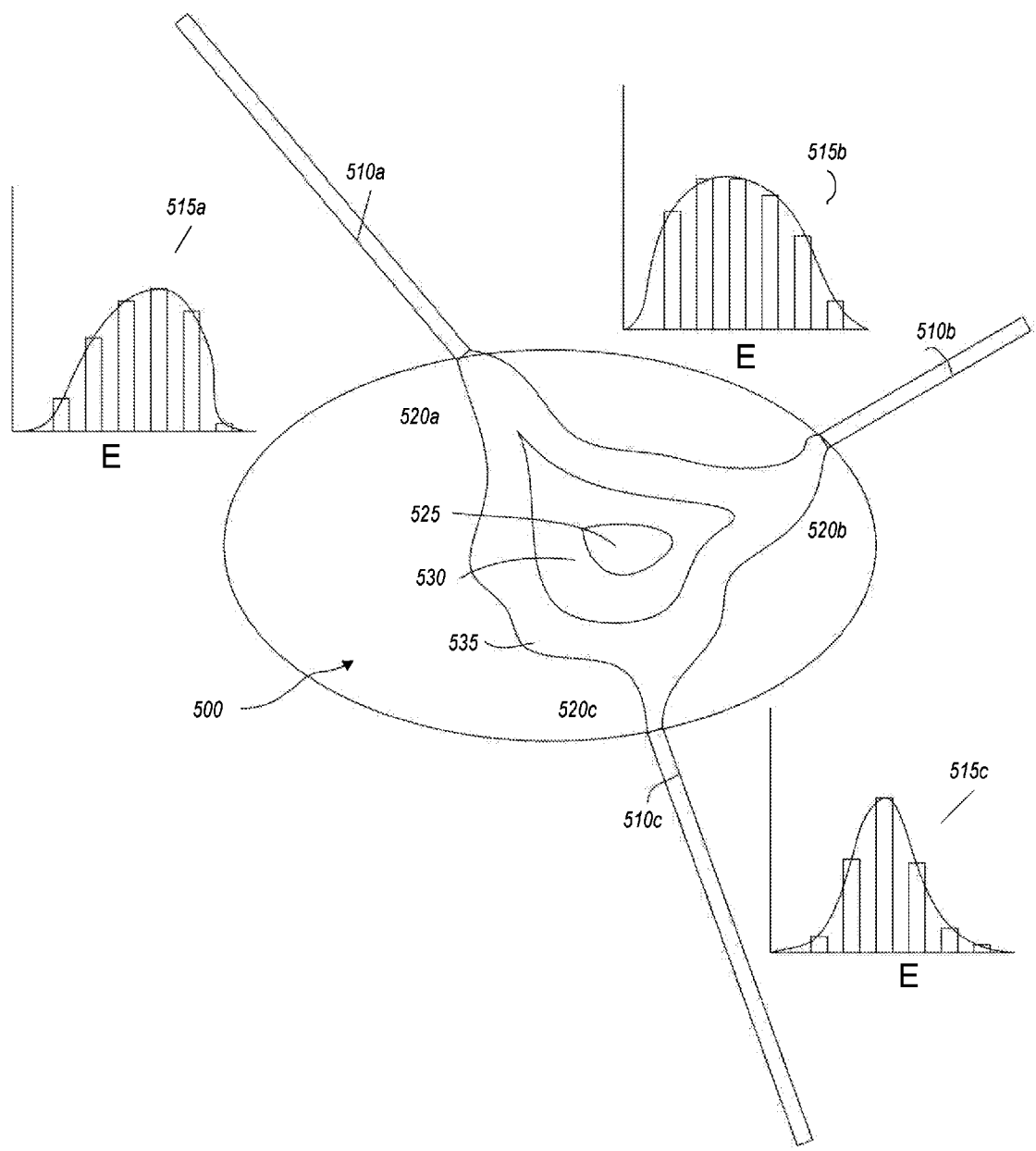
FIG. 5 illustrates an example proton treatment plan according to some implementations.

FIG. 5 illustrates an example proton treatment plan 500 according to some embodiments. The illustration is drawn to emphasize certain features of the proton treatment plan and is therefore not to scale. The proton treatment plan 500 shows a dose distribution 505 created by three proton beams 510a-c. The three proton beams 510a-c have energy distributions 515a-c that create SOBPs 520a-c. The energy distributions 515a-c can be continuous or discrete, as shown. The SOBPs 520a-c from each proton beam 510a-c overlap to create the dose distribution 505 having areas of relatively high dose 525, areas of relatively little dose 530, and areas that receive no dose 535. The area of high dose 525 can be configured to coincide with a target volume (not shown), and the areas of little dose 530 and no dose 535 can be configured to coincide with tissue with sub-clinical disease, normal tissue, organs at risk, or other tissue (not shown).

In block 435, the proton therapy system delivers protons according to a selected proton treatment plan. In some implementations, the proton therapy system automatically selects the proton treatment plan according to desired, defined, default, or selected criteria. For example, the system can automatically select the proton treatment plan that delivers the maximum dose to the target volume while the maximum dose to any organ at risk is below a defined threshold. As another example, the system can automatically select the proton treatment plan that delivers a dose to one or more organs at risk that is below a threshold dose while the minimum dose to the target volume exceeds a defined threshold. In some implementations, the proton therapy system selects a proton treatment plan based at least in part on input from a user. For example, the proton therapy system can present to a user treatment plans from which the user can make a selection.

Forward Problem Solver

As described herein, a forward problem solver can be used to calculate dose distributions based at least in part on proton beamlet characteristics. The forward problem solver can be a module in the proton therapy system or in another system. The forward problem solver can be implemented using one or more processors, memory, and computer readable medium. The forward problem solver can be configured to produce a solution to a forward problem in near real-time.

Figure 6:
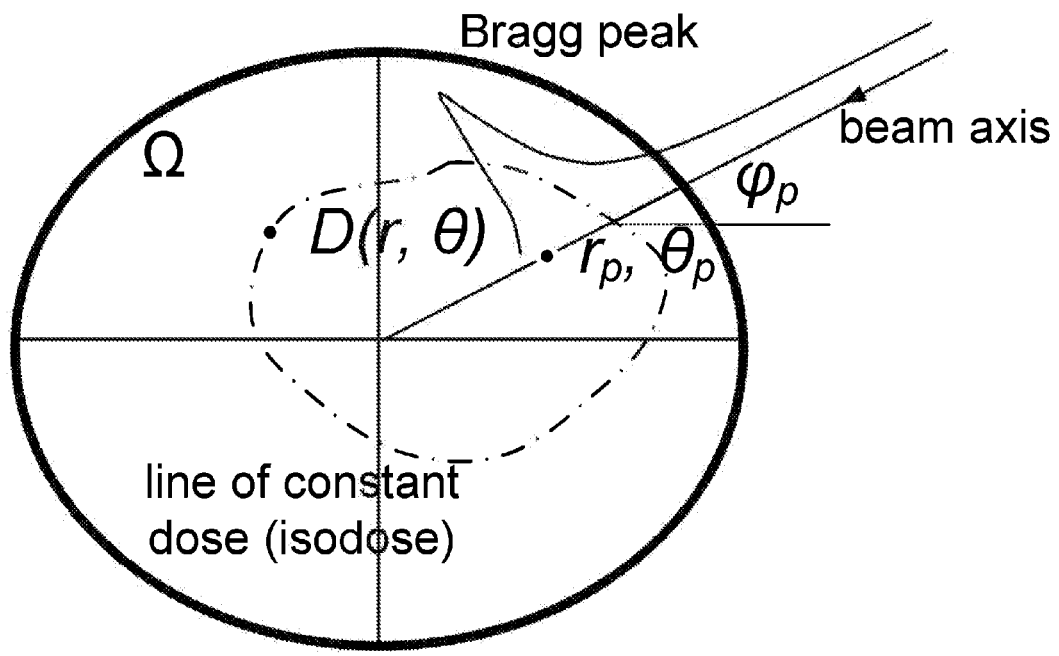
FIG. 6 illustrates a definition of a forward problem according to some implementations of a proton therapy system.

In proton therapy, a forward problem can comprise calculating an output dose based at least in part on an input proton beamlet. The problem can be set forth as follows: given a radiation intensity function of proton beamlets, find the dose function for a cross-section within an object. Referring to FIG. 6, a proton beamlet can be represented by a real-valued function $\rho_p(r_p, \phi_p, \theta_p)$, where $r_p$, $\theta_p$ is the location of the Bragg peak on the beam axis, $\phi_p$ is the angle of the beam axis with the 0-degree axis of the coordinate system, and $\rho_p$ is the intensity of the beam. A dose in the central beam axis plane, defined on a known object cross-section $\Omega$, can be represented by the real-valued, non-zero function $D(r, \theta)$, represented in polar coordinates. Thus, the forward problem comprises finding $D(r, \theta)$ for all $(r, \theta)$ within the cross-section $\Omega$, or $D(r, \theta) = \Delta[\rho_p(r_p, \phi_p, \theta_p)](r, \theta)$ where $\Delta$ is the dose operator that relates the dose function to the radiation intensity function. The dose operator generally is not represented by a closed-form analytic relation between the intensity function and the dose function. In some embodiments, a forward problem solver can be configured to calculate the dose function, D, from the intensity function, $\rho$.

In some embodiments, the forward problem solver incorporates characteristics of proton beamlets to calculate the dose function, D. For example, the forward problem solver can include the absorbed distribution of protons in water in the calculations. The forward problem can include the cylindrical symmetry of the dose distribution around the central beam axis, as another example. Furthermore, the forward problem solver can include the shape of the central beam axis dose distribution, the Bragg peak curve as described herein with reference to FIG. 2A. As another example, the forward problem solver can model the lateral dose profile as a Gaussian function with a depth-dependent width, and can include non-Gaussian tails. As another example, the forward problem solver can scale the beamlet dose profiles linearly with the beam intensity or proton fluence. In some embodiments, the forward problem solver scales the profiles of the proton beamlets for non-uniform tissues that may be different from water. For example, the forward problem solver can scale the profiles according to the relative stopping power and/or relative scattering power of the tissue. By combining the doses from proton beamlets to be used in a proton treatment plan, the forward problem solver can calculate the dose distribution of a complete proton treatment plan.

Inverse Problem Solver

As described herein, an inverse problem solver can be used to calculate a proton beam configuration that delivers a prescribed dose to an object. The inverse problem to be solved for a proton therapy system can be more complex than the inverse problem in other radiation therapy systems because there are a greater number of degrees of freedom due to the capability of a proton system to configure the depth of the Bragg peak of a proton beamlet by selecting a particular energy. Thus, approaches to solving the inverse problem for proton therapy systems can involve comparatively more computational resources, optimization routines, or solution strategies. As a result, solutions to the inverse problem for proton therapy systems can provide relatively higher dose conformity and tumor control probability and lower integral dose and normal tissue complication probability compared to other radiation therapy systems.

The inverse problem solver can be a module in the proton therapy system or in another system. The inverse problem solver can be implemented using one or more processors, memory, and computer readable medium. In some implementations, the inverse problem solver can be configured to produce a solution to an inverse problem in near real-time.

In proton treatment planning systems, the inverse problem comprises calculating feasible proton beam configurations that result in dose distributions that satisfy dose constraints. If $D(r, \theta)$ represents a prescribed dose function in a known cross-section $\Omega$ of an object, then the inverse problem comprises finding a radiation intensity function $\rho_p(r_p, \phi_p, \theta_p)$ such that $\rho_p(r_p, \phi_p, \theta_p) = \Delta^{-1}[D(r, \theta)]$ where $\Delta^{-1}$ is the inverse dose operator that relates the radiation intensity function to the dose function.

Figure 7:
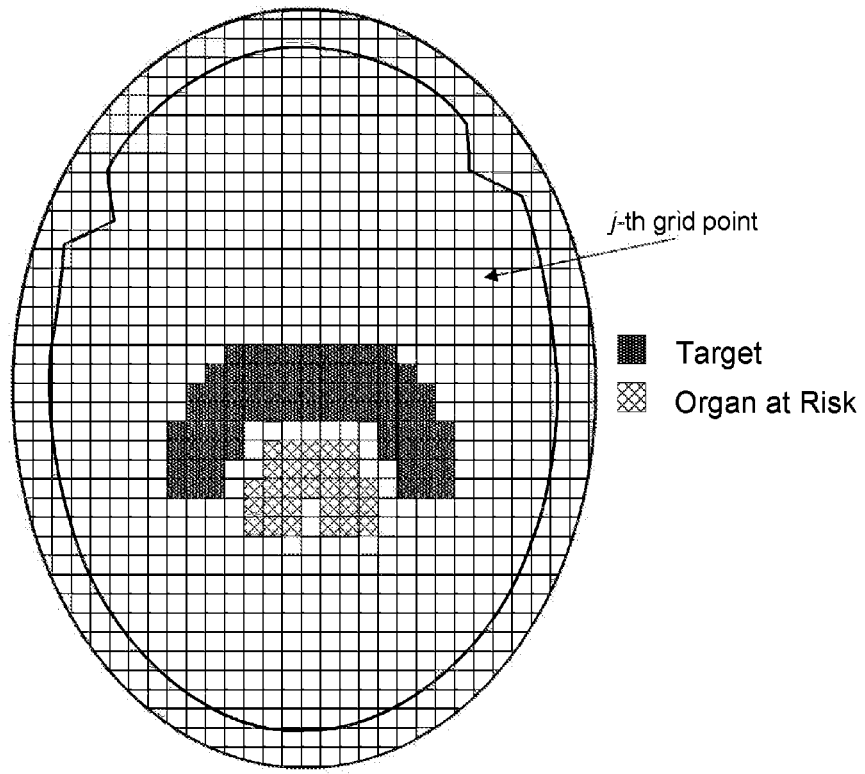
FIG. 7 illustrates an example of a discrete approach to solving an inverse problem, wherein the inverse problem includes calculating proton beam configurations that deliver desired dose distributions.

The inverse problem solver can be implemented using a discrete model. Referring to FIG. 7, the discrete model includes dividing an object cross-section into a discrete grid of dose calculation points. In some embodiments, the discrete grid points represent voxels in the object. From the grid, a number of dose calculation points are chosen for which a dose will be calculated. For example, the inverse problem solver can select J points represented by the polar-coordinate pairs $(r_j, \theta_j)$, where j goes from 1 to J. In addition, the discrete model can include defining a discrete grid of beam aiming points within the target and a discrete grid of beam directions, from which the inverse problem solver selects a number of beamlets. For example, the inverse problem solver can select I beamlets represented by the triplets $(r_i, \phi_i, \theta_i)$ where i goes from 1 to I. In some implementations, the discrete grid of beam directions is equally spaced. In some implementations, the grid of dose calculation points differs from the gird of beam aiming points.

The discrete inverse problem can be set forth by defining $a_{ij}$ to be the dose delivered by the i-th beamlet of unit intensity (or proton fluence) to the j-th dose grid point or voxel. In addition, $x_i$ can be defined as the actual intensity of the i-th beamlet, or the solution the inverse problem solver is seeking. Furthermore, $b_j$ can be defined as the prescribed dose to the j-th dose grid point. As such, the discretized inverse problem becomes finding a proton beamlet vector $x^*$ that solves the linear problem:

$$A^T x^* = b, \text{ where } x^* \geq 0 \tag{1}$$

where the matrix $A^T$ comprises doses of the I unit intensity beamlets to the J object grid points. In some implementations, the inverse problem solver can use a continuous model to solve the inverse problem. For example, the discrete vectors x and b can be represented as two- or three-dimensional functions of proton beam intensities, $x(r)$, and prescribed doses, $b(r)$, and the matrix $A^T$ can be represented as an operator A that operates on the function $x(r)$ to transform the beam intensities function, $x(r)$, into the prescribed dose function $b(r)$.

In some embodiments, the inverse problem solver can use a forward problem solver to calculate the elements of the matrix A. For example, the forward problem solver can calculate a dose to a specified grid point or voxel within the object cross-section based at least in part on a proton beamlet having unit intensity and having a triplet $(r_i, \phi_i, \theta_i)$ representing the location of the Bragg peak in polar coordinates and the beam direction, as described more fully herein above. Thus, the inverse problem solver can construct the matrix A for permutations of dose grid points and beamlets using the forward problem solver.

The grid for the beam aiming points can be the same size as, finer than, or coarser than the grid of dose calculation points. In some embodiments, the size of the grid of beam aiming points is related to the size of the proton beamlets. For example, the size of the grid of beam aiming points can be related to the lateral penumbra of a proton beamlet, where the lateral penumbra can be defined as the lateral extent of a dose from a central beam axis.

In some embodiments, the inverse problem solver can select a limited quantity of fixed beam directions to reduce the complexity of the problem. For example, the inverse problem solver can select at least 1 beam direction and/or less than or equal to 50 beam directions, at least 2 beam directions and/or less than or equal to 25 beam directions, at least 3 beam directions and/or less than or equal to 10 beam directions, or at least 4 beam directions and/or less than or equal to 8 beam directions. For each beam direction, the proton therapy system can direct the beam to the beam aiming point by magnetic scanning, mechanical scanning, moving the patient relative to the beam spot, or using other suitable techniques or combination of techniques.

Method of Solving an Inverse Problem

Figure 8:
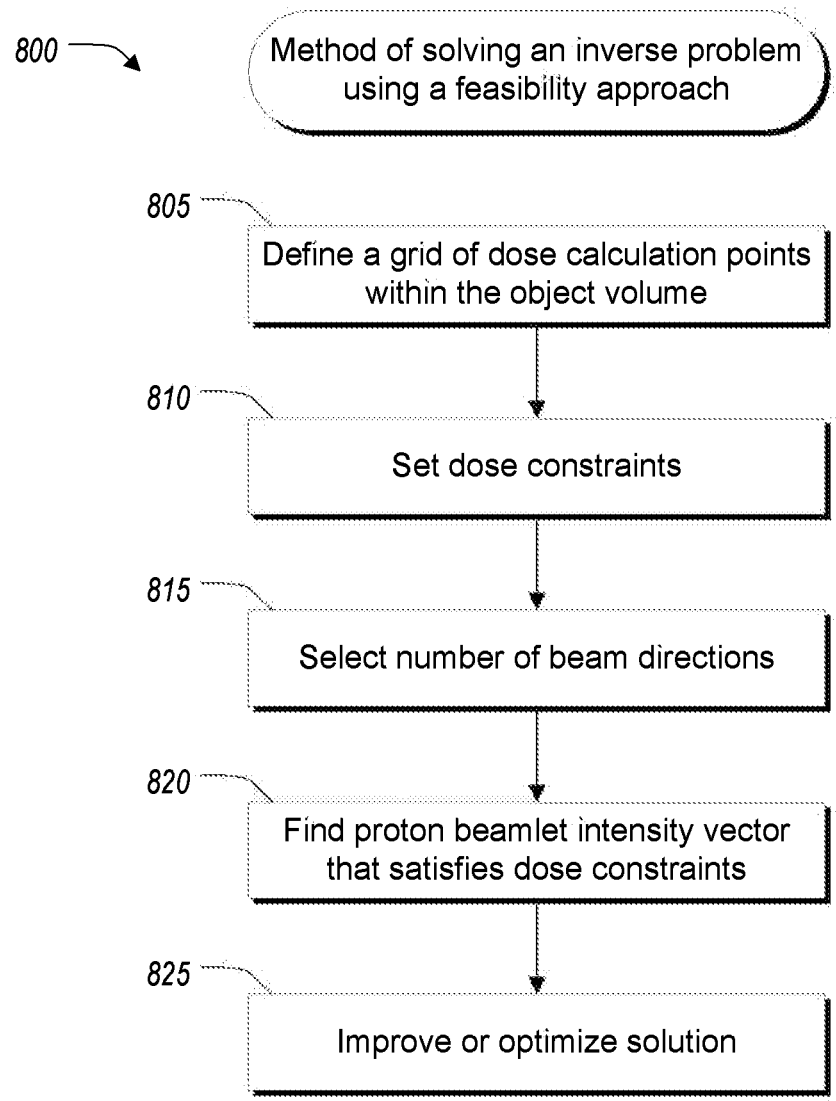
FIG. 8 illustrates a flow chart of an example method of solving an inverse problem using a feasibility approach with dose constraints.

FIG. 8 illustrates a flow chart of an example method 800 of solving an inverse problem using a feasibility approach. The feasibility approach alters equation (1) above to be a pair of inequalities representing upper and lower dose bounds. The equation (1) thus becomes:

$$\underline{D} \leq A^T x^* \leq \overline{D}, \text{ where } x^* \geq 0 \quad (2)$$

where $\underline{D}$ is a vector representing lower dose bounds and $\overline{D}$ is a vector representing upper dose bounds. Any solution to the above inequalities is deemed a feasible solution by the inverse problem solver. The upper and lower dose bounds can be prescribed by the proton therapy system and/or selected by a user. As such, any resulting treatment plan based on a feasible solution could be implemented by the user as it conforms to the prescribed dose constraints.

In block 805, the inverse problem solver defines a grid of dose calculation points within the object volume. In some embodiments, the grid points are voxels within the object volume. As described above with reference to FIG. 7, the grid of dose calculation points represents discrete points in an object cross-section for which a dose calculation will be made. Additionally, the inverse problem solver can define beam aiming grid points in the object cross-section. The beam aiming grid points can coincide with the dose calculation grid points or they can be finer or coarser.

In block 810, the inverse problem solver sets dose constraints. In some embodiments, the dose constraints are set automatically by the inverse problem solver based at least in part on biological, physical, geometrical, and/or physiological information. In some embodiments, the dose constraints are set according to input received from a user. For each dose grid point or voxel defined in block 805, a dose constraint can be set by the inverse problem solver. In some embodiments, an upper dose constraint, lower dose constraint, or both is set for each dose grid point. In some embodiments, the dose constraints are grouped according to volumes and/or sub-volumes of interest. For example, the inverse problem solver can set dose constraints uniformly for dose grid points that fall within the same target sub-volume, target volume, organ at risk sub-volume, organ at risk volume, remaining volume, or other volume.

In block 815, the inverse problem solver selects a number of beam directions. The inverse problem solver can select the beam directions based at least in part on a configuration of proton beams of a therapy system, patient positioning, efficiency considerations, practical considerations, computational considerations, or any combination of these. In some embodiments, the inverse problem solver selects the beam directions based at least in part on input received from a user. The selection of beam directions can reduce the complexity of the inverse problem. Reducing the complexity can result in faster computational times and fewer possible treatment plans for a user or physician to review.

In block 820, the inverse problem solver finds a proton beamlet intensity vector x* that satisfies the dose constraints. For example, where there are J dose grid points and/proton beamlets, the problem can be expressed as:

$$\underline{D}_j \leq \Sigma_{i=1,\ldots,I} a_{ij} x_i \leq \overline{D}_j, j=1,2,\ldots J \text{ and } 0 \leq x_i \leq x_{max}, i=1, 2, \ldots I \quad (3)$$

where the subscript j refers to a dose grid point or voxel and the subscript i refers to a proton beamlet.

In some embodiments, the inverse problem solver can be configured to find a proton beamlet intensity vector x* that satisfies groups of constraints. If G is defined as the set of all dose grid points or voxels, subsets of G can be defined such that the inverse problem solver assigns dose constraints for each subset. For example, $B_l$ can be a subset of G representing L organs at risk, where l=1, 2, . . . L. Dose constraints can be assigned to each organ at risk, or $B_l$, and can be represented by upper dose constraint $\overline{b}_l$ and lower dose constraint $\underline{b}_l$. In some embodiments, $\overline{b}_l$ is greater than or equal to zero and $\underline{b}_l$ is zero. As another example, $T_q$ can be a subset of G representing Q target volumes, where q=1, 2, . . . Q. Dose constraints can be assigned to each target volume, or $T_q$, and can be represented by upper dose constraint $\overline{t}_q$ and lower dose constraint $\underline{t}_q$. In some embodiments, both $\overline{t}_q$ and $\underline{t}_q$ are greater than zero. As another example, C can be a subset of G representing a remaining volume at risk, e.g., dose grid points that are neither part of $B_l$ nor $T_q$. Dose constraints can be assigned to the remaining volume at risk, or C, and can be represented by upper dose constraint $\overline{c}$ and lower dose constraint $\underline{c}$. In some embodiments, $\overline{c}$ is greater than or equal to zero and $\underline{c}$ is zero. The inverse problem solver can be configured to solve an inverse problem similar to equation (3) with an inequality incorporating the corresponding constraints for each defined subset.

In some embodiments, one or more of the organs at risk in the subset $B_l$ can be divided into sub-volumes. Dividing organs at risk into sub-volumes can enable more efficacious proton treatment plans by reducing the integral dose to normal tissue and providing greater control over dose distributions in proton therapy. Organ at risk sub-volumes can be defined, for example, according to biological parameters, physiological parameters, geometrical considerations, relative positioning of structures, practical considerations, or any combination of these.

Figure 9:
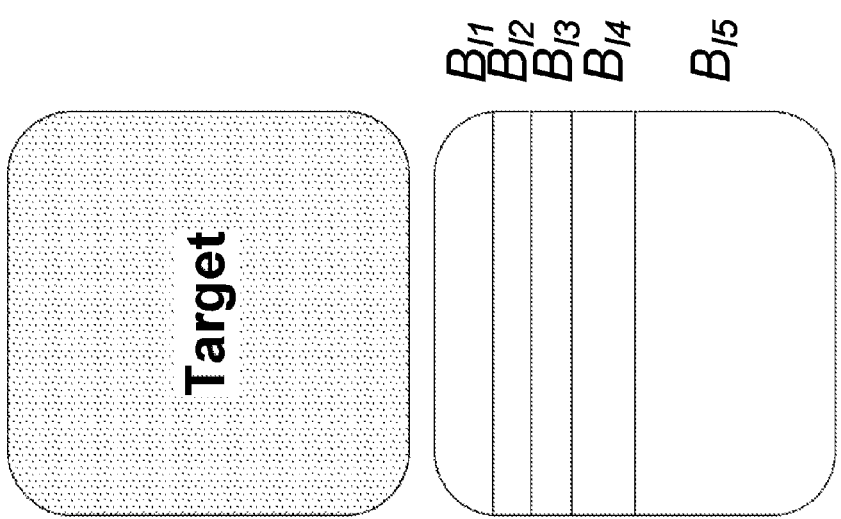
FIG. 9 illustrates an example of dividing an organ at risk into sub-volumes based at least in part on fractional sub-volumes wherein a closest target volume is identified.

In some embodiments, an organ at risk is divided into sub-volumes comprising non-overlapping, relative fractional volumes, the sub-volumes being defined based at least in part on distance relative to a feature of interest, such as a target volume. Referring to FIG. 9, an example procedure to divide an organ at risk $B_l$ into sub-volumes can include identifying a target volume $T_q$ that is the closest target volume to the organ at risk. A number $S_l$ of non-overlapping, fractional sub-volumes $f_{ls}$, where s=1, 2, . . . $S_l$, can be defined for the organ at risk such that each fractional volume $f_{ls}$ is less than one and the sum of all fractional volumes is equal to one. The sub-volumes can be defined by ordering discrete grid points or voxels within the organ at risk $B_l$ according to their distance from the target volume $T_q$. Subsets can be created using the ordered points such that the first subset contains a number of grid points approximately corresponding to the fraction $f_{ls}$ of the total number of dose grid points within the organ at risk, the second subset contains the fraction $f_2$, and so on. In some embodiments, the organ at risk $B_l$ is divided into sub-volumes based at least in part on proximity to a convex hull of any feature of interest, such as target volume $T_q$, not solely based on proximity to the closest target volume. In some embodiments, subsets of the organ at risk $B_l$ are created based at least in part on other criteria, such as, density of tissue, proximity to other organs at risk, patient positioning, beam configuration, uncertainties in proton ranges, uncertainties in positioning of structures, organ movement, or any combination of these.

In some embodiments, one or more target volumes in the subset $T_q$ can be similarly divided into sub-volumes comprising non-overlapping, relative fractional volumes. The division of target volumes into sub-volumes can lead to greater dose conformity, less integral dose, greater tumor control probability, or lower normal tissue complication probability. Target sub-volumes can be defined, for example, at least in part according to biological parameters, physiological parameters, geometrical considerations, relative positioning of structures, practical considerations, or any combination of these.

Figure 10:
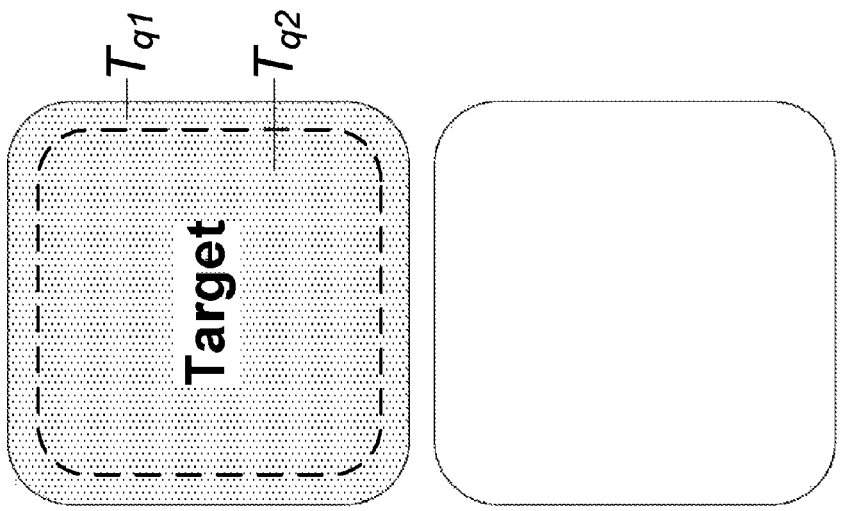
FIG. 10 illustrates an example of dividing a target volume into sub-volumes based at least in part on fractional sub-volumes.

For example, a target volume $T_q$ can be divided into non-overlapping, relative fractional volumes based at least in part on distance to the boundary of the target volume. Referring to FIG. 10, an example procedure to divide a target volume $T_q$ into sub-volumes can include identifying an exterior boundary of the target volume. Prescribed relative fractions $f_{qs}$ can be defined that divide the target volume $T_q$ into $S_q$ non-overlapping sub-volumes, where the fractions $f_{qs}$ are all less than one and sum to one. The sub-volumes can be defined by ordering discrete grid points within the target volume $T_q$ according to the shortest distance to the outer boundary of the target volume. Subsets can be created from the ordered points such that the ratio of the number of grid points in the first subset to the total number of grid points within the target volume is approximately equal to the first prescribed relative fraction, $f_{q1}$. A similar procedure can be repeated for each target sub-volume. In some embodiments, subsets of the target volume $T_q$ are created based at least in part on other criteria, such as, density of tissue, proximity to organs at risk, patient positioning, beam configuration, uncertainties in proton ranges, uncertainties in positioning of structures, organ movement, or any combination of these.

As an example, a target volume $T_q$ can be divided into two sub-volumes. The first sub-volume can include approximately 5% of the total number of grid points or voxels, and the second can contain approximately 95%. The first sub-volume can be referred to as a peripheral fractional volume and can include approximately 5% of the grid points closest to the convex hull of the target volume $T_q$. The second sub-volume can be referred to as a central fractional volume and can include the remaining dose grid points.

A generalized representation of the discrete inverse problem incorporating target and organ at risk sub-volumes can be expressed as follows:

$$\underline{b}_{ls} \leq \Sigma_{i=1 \ldots I} a_{ij} x_i \leq \overline{b}_{ls}, \text{ for all } j \text{ in } B_{ls}, l=1,2,\ldots L \text{ and } s=1,2,\ldots S_l \quad (4a)$$

$$\underline{t}_{qs} \leq \Sigma_{i=1 \ldots I} a_{ij} x_i \leq \overline{t}_{qs}, \text{ for all } j \text{ in } T_{qs}, q=1,2,\ldots Q \text{ and } s=1,2,\ldots S_q \quad (4b)$$

$$\underline{c} \leq \Sigma_{i=1 \ldots I} a_{ij} x_i \leq \overline{c}, \text{ for all } j \text{ in } C \quad (4c)$$

$$0 \leq x_i \leq x_{max}, \text{ for all } i=1,2,\ldots I \quad (4d)$$

where the various underlined and overlined vectors respectively represent lower and upper dose bounds for the corresponding volumes and sub-volumes.

Figure 11:
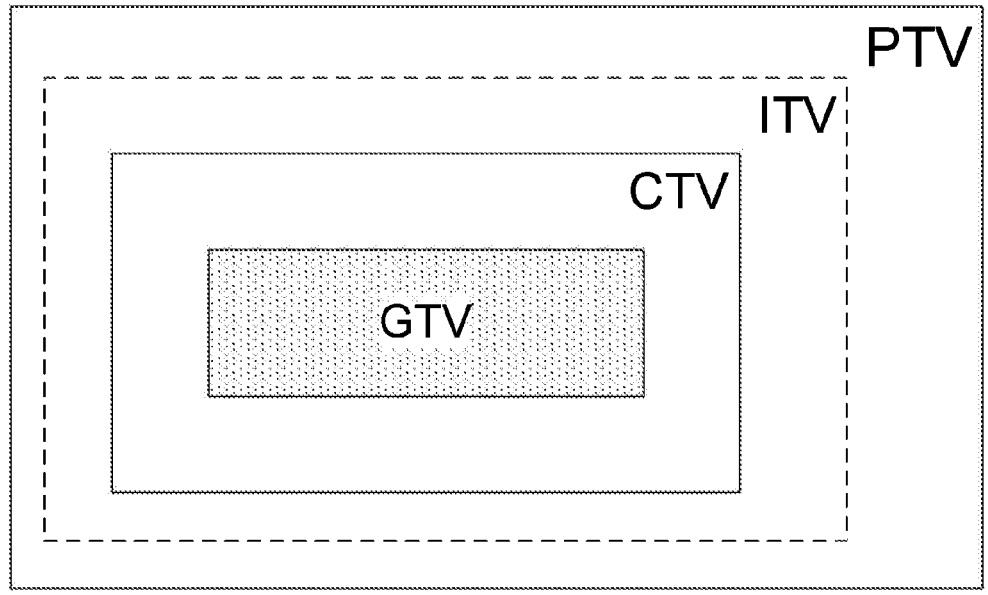
FIG. 11 illustrates examples of target sub-volumes according to standards set by the International Commission of Radiation Units (ICRU).

FIG. 11 illustrates examples of target sub-volumes according to standards set by the International Commission of Radiation Units (ICRU). As described herein, the ICRU has identified and labeled various target volumes based at least in part on clinical considerations, therapeutic goals, and standardized geometrical concepts. The Gross Target Volume (GTV) can include the gross palpable, visible, or demonstrable extent and location of a malignant growth. For example, the GTV can include a primary tumor, metastatic lymphadenopathy, other metastasis, and/or parts of malignant growth where the tumor density exceeds a threshold. In some embodiments, the GTV is determined at least in part using clinical examination and/or imaging techniques. The Clinical Target Volume (CTV) can comprise a tissue volume that includes a GTV and/or sub-clinical microscopic malignant disease which is targeted for elimination. In some embodiments, it is desirable to adequately treat the CTV to achieve removal or palliation of a disease. The Internal Target Volume (ITV) can comprise a volume including a CTV plus an internal margin (IM) configured to compensate for expected physiological movement and variation in size, shape, and position of the CTV during therapy. In some embodiments, the delineation of the ITV is optional. The Planning Target Volume (PTV) can be a geometrical concept that is configured to include a setup margin (SM) around the CTV to account for beam sizes, beam arrangements, geometrical variations, variations in patient positioning, mechanical uncertainties of the equipment, dosimetric uncertainties, transfer set-up errors, human uncertainties, and uncertainties in proton ranges and/or volume location. In some embodiments, the PTV is configured to increase or maximize a probability that a prescribed dose is absorbed by the CTV.

Figure 12:
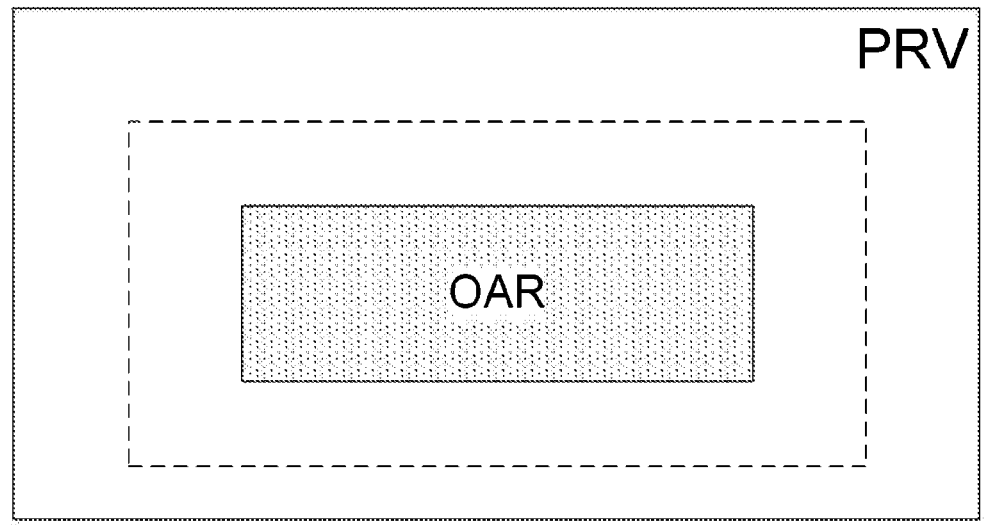
FIG. 12 illustrates examples of organ at risk sub-volumes according to standards set by the ICRU.

FIG. 12 illustrates examples of organ at risk sub-volumes according to standards set by the ICRU. An Organ at Risk (OAR) can comprise normal tissue whose radiation sensitivity may significantly influence treatment planning and/or prescribed dose. A Planning Organ at Risk Volume (PRV) can comprise a volume including the OAR plus volume to account for OAR movement, OAR shape, OAR size, setup margins (SM), and/or internal margins (IM). In some embodiments, the PTV and the PRV overlap.

Uncertainties contribute to the size of the PTV and PRV sub-volumes. For example, volumes of interest can vary with time, including intrafractional variations due in part to internal or external motion and interfractional variations due in part to different patient positioning, different equipment positioning, tumor regression, and/or patient weight loss. In some embodiments, uncertainties can be reduced through motion management techniques and/or frequent imaging and adaptation to updated information about the volumes of interest. As another example, proton range uncertainties can contribute to the size of PTV and PRV sub-volumes. Uncertainties in proton range can arise in part due to systematic stopping power conversion uncertainties, intra- and interfractional motion, relative scattering power uncertainties, or any combination of these. These uncertainties can be specific to a particular proton beam and therefore can be characterized for each beam.

Additionally, other dose volumes can be delineated according to ICRU standards. For example, the Treated Volume (TV) can comprise a volume enclosed by an isodose surface selected by a radiation oncologist, operator, user, physician, dosimetrist, physicist, or technician as appropriate to achieve at least one purpose of treatment. The TV may coincide with the PTV, it may be larger than the PTV, or it may be smaller. As another example, the Irradiated Volume (IV) can comprise a volume that receives a dose that is significant in relation to normal tissue tolerance. A Conformity Index (CI) can comprise the ratio of the TV to the PTV. In some embodiments, the CI can be used as a cost function in optimization processes, as described more fully herein.

Returning to block 825 in FIG. 8, the inverse problem solver improves or optimizes the solution found in block

820. Any solution found in block 820 can be defined as a feasible solution because it satisfies the prescribed dose constraints. In some embodiments, there are multiple feasible solutions to equation (3) and/or equations (4a)-(4d). Among the one or more feasible solutions, it can be advantageous to find a solution that enhances one or more aspects or goals of a therapeutic treatment. In some embodiments, the inverse problem solver can attempt to find an improved or optimized solution among the feasible solutions. An improved or optimized solution can be defined as a solution that enhances or optimizes one or more desirable features, such as, for example, increasing or maximizing the tumor control probability, reducing or minimizing the normal tissue complication probability, increasing or maximizing dose conformity, reducing or minimizing integral dose, increasing or maximizing dose to a target volume, reducing or minimizing dose to an organ at risk, or any combination of these. As described more fully herein, the inverse problem solver can use techniques to improve or optimize solutions that include reducing or minimizing cost functions, reducing or minimizing functions of linear weighted sums, using Pareto optimality to choose weighting factors, defining min-max dose functions, or any combination of these.

Methods to Improve or Optimize Feasible Solutions

Figure 1B:
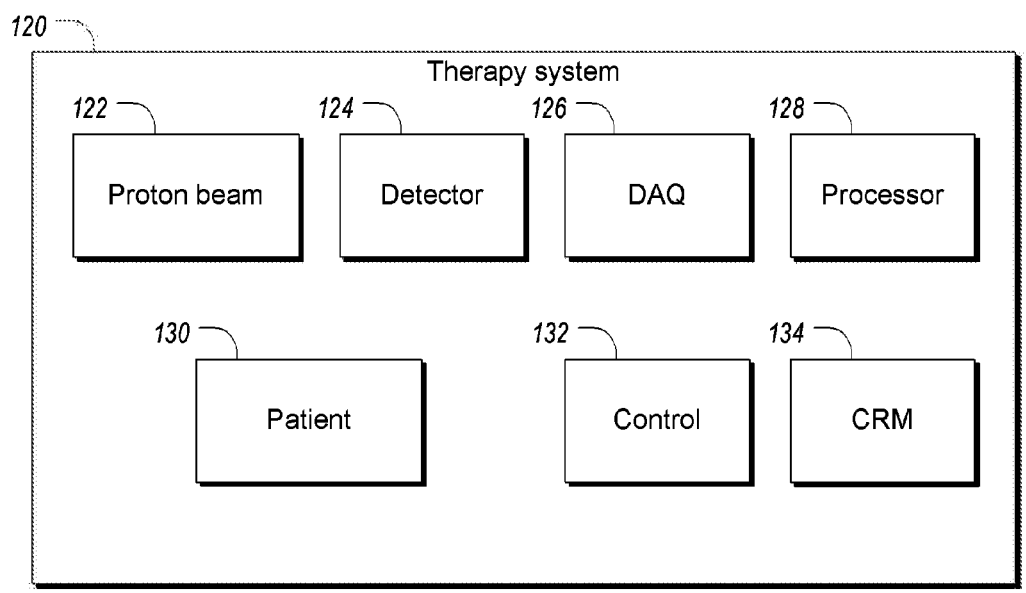
FIG. 1B schematically illustrates that in some implementations, a pCT system can be configured to facilitate treatment of patients using a proton therapy system.

A proton therapy system, such as the therapy system 120 described herein with reference to FIG. 1B, can be configured to improve or optimize feasible solutions to an inverse problem in creating a treatment plan. The feasible solutions represent beamlet intensity vectors satisfying dose constraints imposed by the system, operator, technician, physician, dosimetrist, oncologist, physicist, user, or any combination of these. The improved or optimized solution can be used in formulating a proton treatment plan. In some embodiments, the proton therapy system includes one or more modules configured to improve or optimize feasible solutions. The feasible solutions can be obtained through a forward problem solver module, an inverse problem solver module, a proton treatment planning system, an IMPT planning system, or any combination of these. The modules or systems that provide feasible solutions can be part of the proton therapy system or separate from it. In some embodiments, an inverse problem solver produces and reports feasible solutions obtained according to the process 800 described herein.

Figure 13:
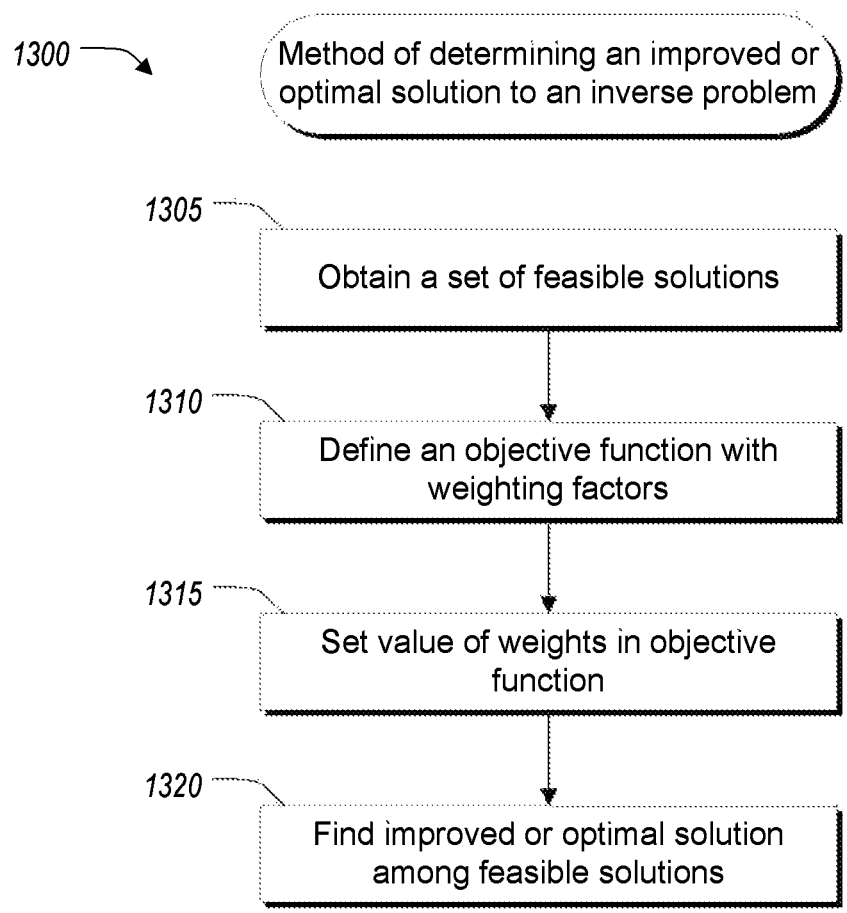
FIG. 13 illustrates a flow chart of an example method for determining an improved or optimized solution from a set of feasible solutions of an inverse problem.

FIG. 13 illustrates a flow chart of an example method 1300 for determining an improved or optimized solution from a set of feasible solutions of an inverse problem. In block 1305, the therapy system obtains a set of feasible solutions. The feasible solutions can be solutions to an inverse problem with prescribed dose constraints as found in equations (3) and (4a)-(4d). The feasible solutions can represent proposed beamlet intensity vectors that would result in a dose delivered to a patient or object that would satisfy prescribed dose constraints. In general, any of the feasible solutions could be implemented without violating the dose constraints. In some embodiments, it can be desirable to find a solution that enhances, improves, reduces, increases, maximizes, minimizes, or optimizes certain therapeutic goals. Thus, the proton therapy system can be configured to find an improved or optimized solution among the obtained feasible solutions that accomplishes the above desire.

In block 1310, the therapy system sets an objective function with weighting factors for use in the improvement or optimization method. The objective function can be defined to operate over the space of intensity vectors or the space of dose vectors. For example, the problem to be solved can take one of the following forms:

$$\min f(x) \, s.t. \, \underline{D}_j \leq A^T x \leq \overline{D}_j, j=1,2,\ldots J \text{ and } 0 \leq x_i \leq x_{max}, \\ i=1,2,\ldots I \quad (5)$$

$$\min g(A^T x) \, s.t. \, \underline{D}_j \leq A^T x \leq \overline{D}_j, j=1,2,\ldots J \text{ and } 0 \leq x_i \leq x_{max}, \\ i=1,2,\ldots I \quad (6)$$

where $f(x)$ and $g(A^T x)$ are objective functions. In some implementations, the objective function is automatically selected by the proton therapy system. In some implementations, the objective function is set by the therapy system using input from a user. The objective function can be a biological or physical cost function that is to be reduced or minimized, or a biological or physical utility function that is to be increased or maximized. For example, the conformity index, defined as the ratio of the TV to the PTV, can be used as a cost function in the procedure.

In some implementations of the method 1300, the objective cost function is a linear weighted sum. For example, the objective function can be defined as operating over the space of dose vectors:

$$g(A^T x) = \Sigma_{j \in B \cup C}(A_j)^T x - \Sigma_{i \in T} w_j (A_j)^T x \quad (7)$$

where $w_j$ are relative weights of importance that can be grouped according to organs at risk, B, remaining volume at risk, C, and target volumes, T. Using equation (7) as the objective function in equation (6) can result in a reduction or minimization of the weighted sum of normal tissue doses (the first term in equation (7)) and the negative sum of tumor doses (the second term in equation (7)).

In some implementations of the method 1300, the objective cost function is a sum of min-max dose functions. For example, the objective function can be defined as operating over the space of dose vectors:

$$g(A^T x) = \max_{j \in B \cup C}\{w_j (A_j)^T x\} - \min_{i \in T}\{w_j (A_j)^T x\} \quad (8)$$

where $w_j$ are relative weights of importance that can be grouped according to organs at risk, B, remaining volume at risk, C, and target volumes, T. Using equation (8) as the objective function in equation (6) can result selecting among the feasible solutions the solution that increases or maximizes a lowest target dose and decreases or minimizes a highest normal tissue dose.

In block 1315, the therapy system sets the weights used in the objective functions. In some implementations, the weights can be selected automatically by the therapy system. In some implementations, the proton therapy system sets the weights based at least in part on input from a user. In some embodiments, the objective function can take the general form:

$$g(A^T x) = g_{B \cup C}(A^T x, w_{B \cup C}) + g_T(A^T x, w_T) \quad (9)$$

where the weights $w_{B \cup C}$ and $w_T$ are applied to normal tissue and target volumes, respectively. The objective function in equation (9) allows the system to present simplified options for improving or optimizing feasible solutions. For example, the therapy system can select a combination of weights that enhances certain therapeutic aspects, such as favoring the importance of normal tissue sparing, the importance of maximum tumor control, or giving equal importance to both. In some embodiments, this is accomplished through the use of weights that are Pareto optimal or efficient. A solution, $x^*$, is Pareto optimal or efficient for an objective function of the form in equation (9) if there is no other feasible solution, x, such that $g_T(A^T x, w_S) \leq g_T(A^T x^*, w_S)$, where s=1, 2 with a strict inequality for at least one s. The Pareto optimal solution thus represents a situation where a reduction in the value of either partial objective function increases the value of the other one.

In block 1320, the therapy system finds the improved or optimal solution among the feasible solutions by finding a minimum or maximum of the objective function. Finding the minimum or maximum of the objective function can include using an iterative, analytic, mathematical, numerical, or similar approach to find a local or global minimum or maximum of the objective function. In some embodiments, finding the minimum or maximum includes finding a solution that decreases or increases the objective function below or above a threshold.

Dose Prescription

Figure 14:
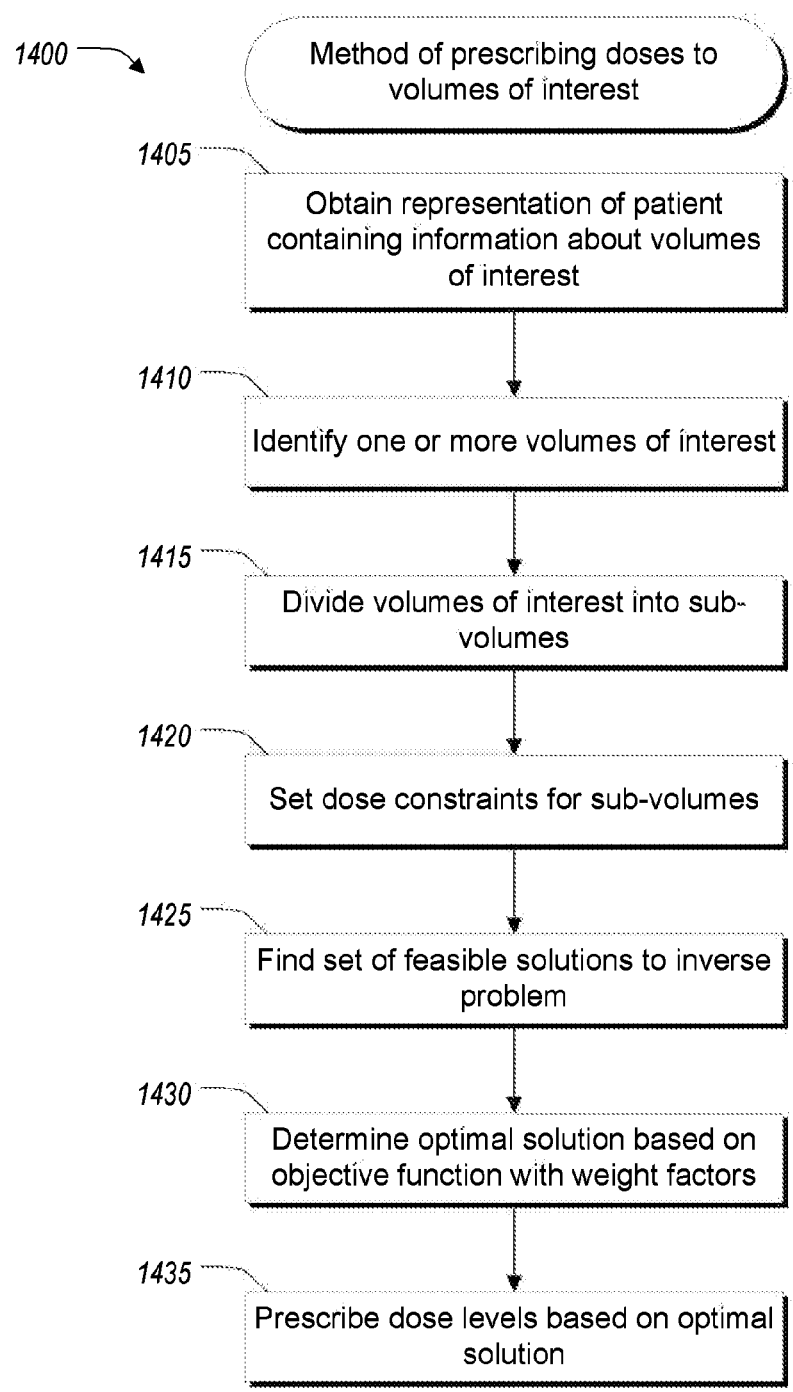
FIG. 14 illustrates a flow chart of an example method for prescribing doses to volumes and sub-volumes in a patient or object.

FIG. 14 illustrates a flow chart of an example method 1400 for prescribing doses to volumes and sub-volumes in a patient or object. Prescribing dose constraints to the various volumes and sub-volumes of interest can be complicated due to overlapping volumes and sub-volumes. In some implementations, the proton therapy system or a physician, dosimetrist, oncologist, physicist, user, operator, technician or the like can set dose constraints and choose a proton treatment plan based at least in part on several criteria, including tumor control probability, dose conformity, uniformity of a dose to a target volume, dose delivery to targeted sub-volumes, normal tissue complication probability, integral dose, treatment duration, proton beam characteristics, or any combination of these.

In block 1405, the proton therapy system obtains a representation of the object or patient which includes information about the volumes and sub-volumes of interest. As described more fully herein with reference to FIGS. 4 and 8, the proton therapy system can use the representation to, for example, identify volumes of interest, divide volumes of interest into sub-volumes, assess a proposed treatment plan, reduce uncertainties, or any combination of these. The proton therapy system can obtain the representation through the use of functional imaging, including pCT.

In block 1410, the proton therapy system identifies one or more volumes of interest. The proton therapy system can be configured to analyze the representation obtained in block 1405 to identify target volumes, organs at risk, normal tissue, remaining volume at risk, other structures, and the like. In some implementations, the proton therapy system is configured to accept input from a user to identify the volumes of interest. For example, the proton therapy system can present the obtained representation to a user, physician, oncologist, technician, operator, and the like. The user can delineate, identify, and/or label the volumes of interest based at least in part on the obtained representation.

In block 1415, the proton therapy system divides the volumes of interest into sub-volumes. As described herein with reference to FIG. 8, sub-volumes can be defined according to geometrical considerations, biological considerations, physiological factors, equipment characteristics, interfractional variations, intrafractional variations, proton range uncertainties, or any combination of these. In some implementations, the proton therapy system divides a target volume into sub-volumes based at least in part on selected fractional volume values. For example, as described more fully herein, the target sub-volumes can be delineated and identified by creating fractional volumes within the target volume corresponding to proximity to a convex hull of the target volume. In some implementations, the proton therapy system divides the target volume into sub-volumes based at least in part on the ICRU standards described herein with reference to FIG. 11. In some implementations, the proton therapy system divides an organ at risk into sub-volumes based at least in part on selected fractional volume values. For example, as described more fully herein above, the organ at risk sub-volumes can be delineated and identified by creating fractional volumes within the organ at risk based at least in part on a proximity to one or more target volumes. In some implementations, the proton therapy system divides the organs at risk into sub-volumes based at least in part on the ICRU standards described herein with reference to FIG. 12. In some implementations, the proton therapy system divides a target volume or organ at risk into sub-volumes based at least in part on input from a user.

In block 1420, the proton therapy system sets dose constraints for the sub-volumes delineated and identified in block 1415. The system can set dose constraints based at least in part on historical radiation treatment information, sensitivity of tissue to radiation, proximity to target volumes and/or organs at risk, or any combination of these. The system can set the dose constraints automatically or it can set the dose constraints based at least in part on input from an oncologist, dosimetrist, physicist, physician, operator, user, or the like.

In block 1425, the proton therapy system finds one or more feasible solutions to an inverse problem, as described more fully herein with reference to FIG. 8. The proton therapy system can utilize an inverse problem solver module to create a set of feasible solutions such that the module identifies proton beamlet configurations that would deliver doses to the volumes of interest that fall within the dose constraints. If the module does not identify any proton beamlet configuration that would satisfy the dose constraints, the module can inform the proton therapy system. The proton therapy system can then return to any previous point in the process 1400 to alter or remove volumes of interest, to alter or remove sub-volumes, to alter or remove dose constraints, or any combination of these.

In block 1430, the proton therapy system finds an improved or optimal solution from the set of feasible solutions found in block 1425. As described more fully herein with reference to FIG. 13, the proton therapy system can be configured to find an improved or optimal solution that enhances one or more desirable qualities as selected by the proton therapy system and/or a physician, oncologist, user, technician or operator. In some implementations, the proton therapy system finds the improved or optimal solution by reducing or minimizing an objective function, such as a biological or physical cost function. For example, the objective function can be a linear weighted sum similar to equation (7), which can result in a minimization of the weighted sum of normal tissue doses and the negative sum of tumor doses. As another example, the objective function can be a weighted sum of min-max doses similar to equation (8), which can result in selecting among the feasible solutions a solution with a maximum of the lowest target dose and a minimum of the highest normal tissue dose. In some implementations, the proton therapy system finds the improved or optimal solution by selecting weights in the objective function that reflect the relative importance of aspects of proton therapy. For example, the proton therapy system can assign a weight factor for targeted volumes and a weight factor for organs at risk and a remaining volume at risk. The weight factors can be varied such that a Pareto optimal solution is found that enhances normal tissue sparing, tumor control, or a balance of both normal tissue sparing and tumor control. In some implementations, the proton therapy system can utilize other procedures to enhance desired proton therapy results.

In block 1435, the proton therapy system prescribes dose levels according to the improved or optimal solution found in block 1430. The proton therapy system can assign dose levels to the identified sub-volumes based at least in part on the solution identified above. The assigned doses can be used to configure the proton therapy system to produce a specified proton beam configuration for delivery of proton therapy.

Figure 15:
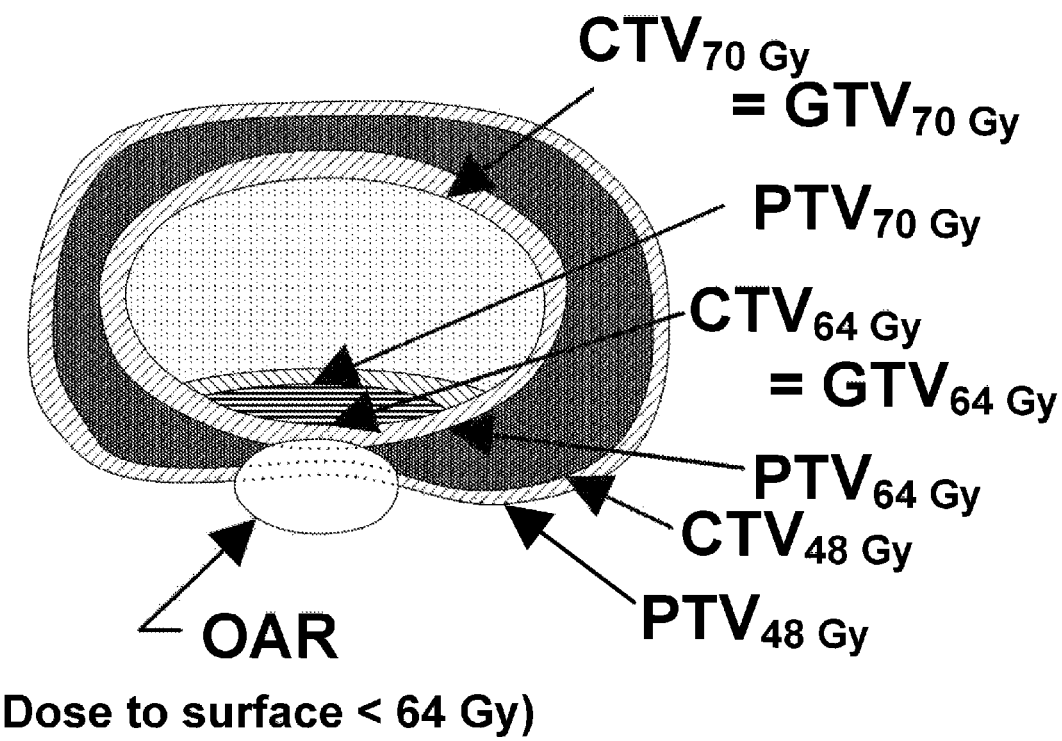
FIG. 15 illustrates an example proton treatment plan prescribed to a patient according to some embodiments described herein.

FIG. 15 illustrates an example proton treatment plan 1500 prescribed to a patient according to some implementations described herein. The proton treatment plan provides for prescribed doses to several volumes of interest identified according to ICRU standards. A majority of a GTV is assigned a dose of 70 Gy, and a fraction of the remaining GTV is assigned a dose of 64 Gy due at least in part to the proximity of that fractional volume to an organ at risk. A CTV containing a sub-clinical level of disease is prescribed a dose of 48 Gy, which is also within the tolerance of an OAR. The OAR is divided into a surface of interest (SOI), which is made up of dose grid points that form its boundary, and inner grid points. The SOI is allowed to receive a maximum dose of 63.9 Gy. Doses are prescribed to all PTVs and a PRV (not shown for clarity) as well.

Example Treatment Plan Assessment

Figure 16:
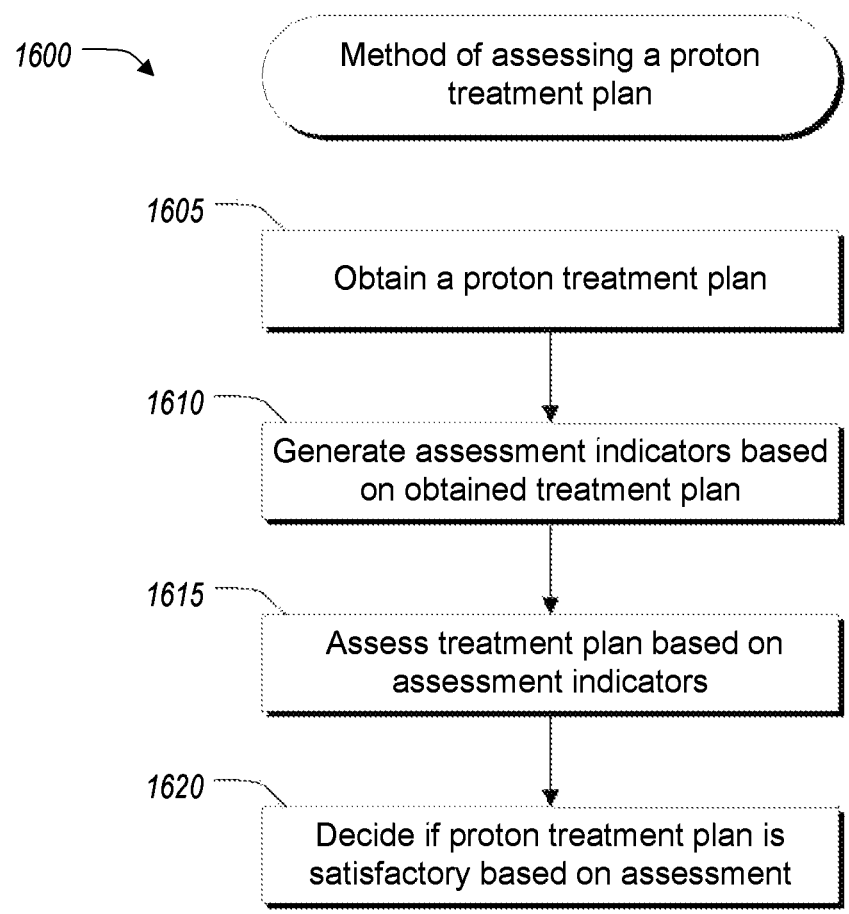
FIG. 16 illustrates a flow chart of an example method for assessing a proton treatment plan derived according to some embodiments described herein.

FIG. 16 illustrates an example method 1600 for assessing a proton treatment plan derived according to some embodiments described herein. The proton therapy system can be configured to assess whether a treatment plan meets prescribed dose constraints. This can provide feedback to the system or a physician so that the treatment plan can be analyzed, altered, and/or executed.

In block 1605, the proton therapy system creates a proton treatment plan, as described herein with reference to FIGS. 4 and 14. The proton treatment plan can include a dose distribution based at least in part on a selected proton beam configuration. In some implementations, the proton therapy system creates and presents a visual representation of the proton treatment plan to a user. In some implementations, the proton treatment plan is based at least in part on an improved or optimal solution obtained according to the methods described herein with reference to FIG. 13.

In block 1610, the proton therapy system generates assessment indicators to evaluate the proposed treatment plan. Assessment indicators can include any metric or representation that provides the system or user with information related to the treatment plan's ability to deliver prescribed doses and/or achieve desired therapeutic goals. In some implementations, the proton therapy system generates assessment indicators including, for example, a dose volume histogram, a conformity index, a dose homogeneity indicator, a tumor control probability, a normal tissue complication probability, a probability of uncomplicated tumor control, or any combination of these.

Figure 17:
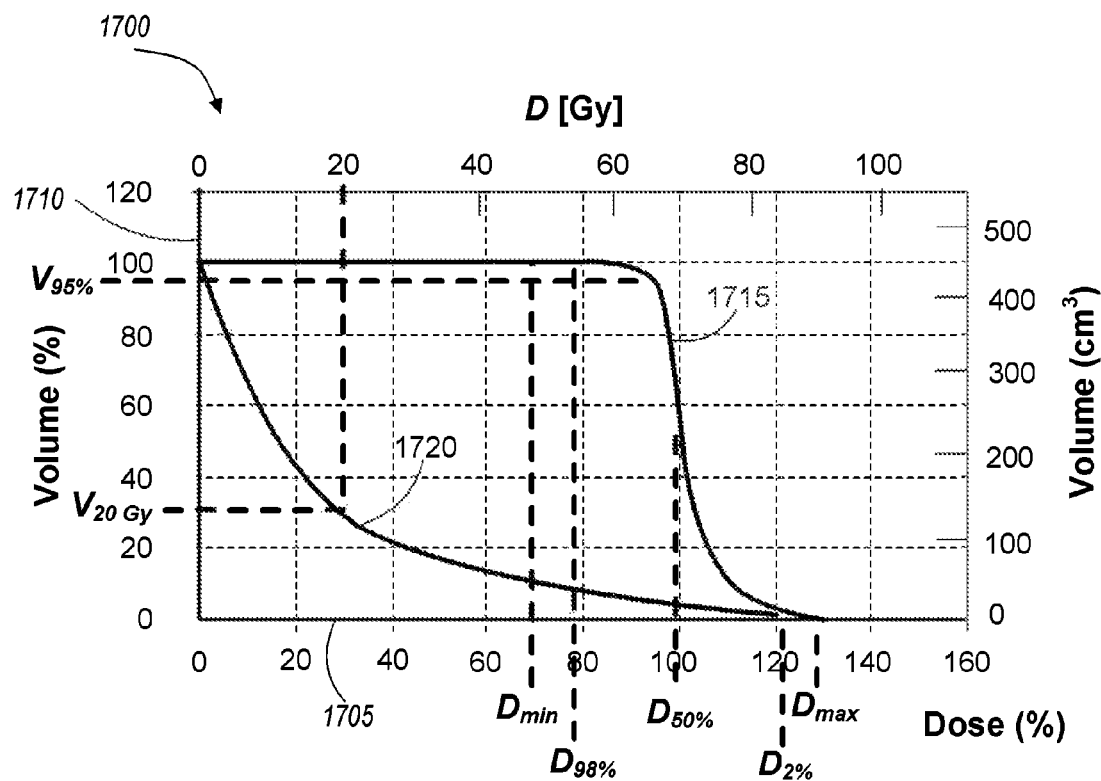
FIG. 17 illustrates a dose volume histogram (DVH) used as an assessment indicator for assessing a proton treatment plan.

FIG. 17 illustrates an example assessment indicator, a dose volume histogram (DVH) 1700. The DVH 1700 can include a plot of a cumulative dose-volume frequency distribution which graphically summarizes the simulated radiation distribution within a volume of interest of a patient which would result from a proposed treatment plan. The DVH 1700 can present information about the uniformity of dose in a specified volume and can be used as an input for calculations of tumor control probability and normal tissue complication probability. Moreover, the DVH 1700 can be used to assess the least dose delivered to a specified volume. The DVH 1700 includes information about the dose on the horizontal axis 1705 and the specified volume on the vertical axis 1710. The DVH 1700 can include dose information for a PTV 1715 (dashed line), PRV 1720 (solid line), or other volume (not shown). The proton therapy system can derive values from the DVH 1700 to assist in the assessment of the treatment plan including, for example, a volume that receives at least a specified dose, $V_D$, a least dose that is received by a specified volume, $D_V$, or both.

A measure of the efficacy of a treatment plan can include the tumor control probability (TCP) which is the probability that no malignant cells are left in a targeted location after irradiation. TCP can be used in conjunction with any targeted tissue, not just with tumors. A measure of the efficacy of a treatment plan can also include the normal tissue complication probability (NTCP) which is a measure of the probability of a complication to normal tissue for a given radiation dose. In treating cancerous cells, for example, it is desirable to achieve a high TCP (close to 1) and maintain the NTCP at an acceptably low level. Another measure of the efficacy of a treatment plan can include the probability of uncomplicated tumor control ($P_{UTC}$) which can be defined as TCP(1-NTCP).

Another assessment indicator can include the conformity index (CI). In some embodiments, the CI is defined as the ratio of the TV to the PTV and can be useful when sub-volumes are defined according to standards set by the ICRU. In some implementations, the CI is used as a cost function in the optimization procedure described more fully herein with reference to FIG. 13.

In block 1615, the proton therapy system assesses the treatment plan based at least in part on the assessment indicators generated in block 1610. Evaluating the efficacy of a treatment plan can include analyzing, calculating, or measuring the dose delivered to targeted tissue and/or non-targeted tissue. Targeted tissue can include cancerous cells, tumors, lesions, or any other tissue.

In block 1620, the proton therapy system decides whether the proposed treatment plan is satisfactory based at least in part on the information obtained by analyzing the assessment indicators. In some implementations, the therapy system can present the assessment information to a user of the system such that the system can receive input from the user regarding whether to implement the treatment plan. In some implementations, the system automatically classifies the treatment plan as satisfactory if one or more assessment indicators surpass a threshold value. In a scenario where the proton therapy system deems the proton treatment plan unsatisfactory, the assessment information can be used to alter the proton treatment plan.

CONCLUSION

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment. Accordingly, no feature or group of features is necessary or indispensable to each embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprise programmable units, such as programmable gate arrays, application specific integrated circuits, and/or processors. The modules described herein may be implemented as software modules, or may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of non-transitory computer-readable medium or other non-transitory computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A method for performing intensity-modulated ion therapy, the method comprising:
    obtaining positional information of structures within or on the patient;
    identifying a feature of interest to be targeted by the ion therapy, the feature of interest comprising at least a portion of a structure within or on the patient;
    identifying a volume of interest that includes the feature of interest, the volume of interest being larger than the feature of interest;
    dividing the volume of interest into a plurality of sub-volumes such that the feature of interest comprises one or more sub-volumes;
    setting a dose constraint for individual sub-volumes;
    generating one or more ion treatment plans that satisfy each of the dose constraints of the individual sub-volumes; and
    delivering ions to the patient using a selected ion treatment plan from the one or more generated ion treatment plans,
    wherein individual sub-volumes comprise a group of voxels that are within a range of defined distances from the feature of interest, the range of defined distances from the feature of interest being different for different sub-volumes.

2. The method of claim 1, wherein delivering ions to the patient comprises delivering protons.

3. The method of claim 1, wherein delivering ions to the patient comprises delivering carbon ions.

4. The method of claim 1, wherein dividing the volume of interest into a plurality of sub-volumes comprises dividing the volume of interest into a grid of dose calculation points.

5. The method of claim 1, wherein setting a dose constraint for individual sub-volumes comprises receiving an input from a user.

6. The method of claim 1, wherein generating one or more ion treatment plans that satisfy each of the dose constraints of the individual sub-volumes comprises using an inverse problem solver to determine ion beam characteristics predicted to deliver radiation doses to the plurality of sub-volumes within the dose constraint.

7. The method of claim 1, wherein the dose constraint comprises a minimum dose constraint.

8. The method of claim 1, wherein the dose constraint is set based at least in part on the range of defined distances from the feature of interest.

9. An intensity-modulated ion therapy system comprising:
    an ion delivery system configured to deliver one or more beams of ions to a patient;
    an ion detector configured to measure a number of ions delivered; and
    one or more physical processors configured to perform the steps of:

obtaining positional information of structures within or on the patient;

identifying a feature of interest to be targeted by the ion therapy, the feature of interest comprising at least a portion of a structure within or on the patient;

identifying a volume of interest that includes the feature of interest, the volume of interest being larger than the feature of interest;

dividing the volume of interest into a plurality of sub-volumes such that the feature of interest comprises one or more sub-volumes;

setting a dose constraint for individual sub-volumes;

generating one or more ion treatment plans that satisfy each of the dose constraints of the individual sub-volumes; and delivering one or more beams of ions to the patient using a selected ion treatment plan from the one or more generated ion treatment plans;

wherein individual sub-volumes comprise a group of voxels that are within a range of defined distances from the feature of interest, the range of defined distances from the feature of interest being different for different sub-volumes.

10. The therapy system of claim 9, wherein the one or more beams of ions comprises a beam of protons.

11. The therapy system of claim 9, wherein the one or more beams of ions comprises a beam of carbon ions.

12. The therapy system of claim 9, wherein the one or more physical processors is further configured to generate one or more ion treatment plans that satisfy each of the dose constraints of the individual sub-volumes comprises using an inverse problem solver to determine ion beam characteristics predicted to deliver radiation doses to the plurality of sub-volumes within the dose constraint.

13. The therapy system of claim 9, wherein the dose constraint comprises a maximum dose constraint.

* * * * *

UNITED STATES PATENT AND TRADEMARK OFFICE
CERTIFICATE OF CORRECTION

PATENT NO. : 9,555,265 B2
APPLICATION NO. : 14/945214
DATED : January 31, 2017
INVENTOR(S) : Reinhard W. Schulte It is certified that error appears in the above-identified patent and that said Letters Patent is hereby corrected as shown below:

In the Specification

In Column 4 at Line 55, change "Imagine" to --Imaging--.

In Column 15 at Line 16 (approx.), change "$\underline{D} \leq A^T x^* \leq \overline{D},$" to --$\underline{D} \leq A^T x^* \leq \overline{D},$--.

In Column 15 at Line 67, change "and/proton" to --and I proton--.

In Column 16 at Line 20 (approx.), change "$\underline{t}_q$" to --$\underline{t}_q$.--.

In Column 16 at Line 60, change "$f_2$," to --$f_{2s}$,--.

In Column 20 at Lines 23-24 (approx.), change

"$g(A^T x) = \Sigma_{j \in B \cup C}(A_j)^T x - \Sigma_{i \in T} w_j (A_j)^T x$" to --$g(A^T x) = \Sigma_{j \in B \cup C} w_j (A_j)^T x - \Sigma_{i \in T} w_j (A_j)^T x$--.

Signed and Sealed this
Twenty-third Day of May, 2017

Michelle K. Lee
*Director of the United States Patent and Trademark Office*